(12) United States Patent
Joyashiki et al.

(10) Patent No.: US 9,216,072 B2
(45) Date of Patent: Dec. 22, 2015

(54) DRUG-CONTAINING PERSONAL HYGIENE IMPLEMENT

(75) Inventors: Hisashi Joyashiki, Takatsuki (JP);
Kazuyuki Uo, Takatsuki (JP); Masato Yamashita, Takatsuki (JP)

(73) Assignee: SUNSTAR INC., Takatsuki-shi (JP)

( * ) Notice: Subject to any disclaimer, the term of this patent is extended or adjusted under 35 U.S.C. 154(b) by 301 days.

(21) Appl. No.: 13/813,521

(22) PCT Filed: Aug. 2, 2011

(86) PCT No.: PCT/JP2011/067712
§ 371 (c)(1),
(2), (4) Date: Jan. 31, 2013

(87) PCT Pub. No.: WO2012/018030
PCT Pub. Date: Feb. 9, 2012

(65) Prior Publication Data
US 2013/0130196 A1    May 23, 2013

(30) Foreign Application Priority Data

Aug. 2, 2010 (JP) ................................ 2010-173731
Aug. 2, 2010 (JP) ................................ 2010-174013

(51) Int. Cl.
*A47L 13/22* (2006.01)
*B43K 5/14* (2006.01)
(Continued)

(52) U.S. Cl.
CPC .................. *A61C 17/005* (2013.01); *A46B 9/04* (2013.01); *A46B 11/0027* (2013.01);
(Continued)

(58) Field of Classification Search
CPC .... A61C 15/00; A61C 17/005; A61B 17/244; A46B 9/04; A46B 11/0041; A46B 15/0081; A46B 17/04; A46B 2200/108

USPC ......... 401/270, 277, 132–134, 183, 184, 269; 433/80, 82, 89, 87; 15/104.93, 167.1
See application file for complete search history.

(56) References Cited

U.S. PATENT DOCUMENTS 4,521,128 A * 6/1985 O'Neal ........................ 401/183
4,572,689 A    2/1986 Chernack
(Continued)

FOREIGN PATENT DOCUMENTS

JP    S64-38169    2/1989
JP    S64-51432    3/1989
(Continued)

OTHER PUBLICATIONS

International Search Report for International Application No. PCT/JP2011/067712 dated Nov. 8, 2011.

*Primary Examiner* — Jennifer C Chiang
(74) *Attorney, Agent, or Firm* — Kratz, Quintos & Hanson, LLP

(57) ABSTRACT

To provide an economical and sanitary drug-containing personal hygiene implement that is easy to produce and manage, and has an excellent portability even when both personal hygiene implement and drug are used away from home.

The drug-containing personal hygiene implement includes a bottle body in which a drug is stored, a personal hygiene body which has a shaft section and a distal-end personal hygiene section, protrudes to a distal-end side of the bottle body, and is used to implement care of a human body, and a passage provided on a distal-end section of the bottle body and guiding the stored drug to the personal hygiene body, the implement being characterized in that opening operation makes it possible for the drug to flow through the passage in the bottle body.

9 Claims, 35 Drawing Sheets

(51) Int. Cl.
    *A61C 17/00*     (2006.01)
    *A61C 15/00*     (2006.01)
    *A61B 17/24*     (2006.01)
    *A46B 9/04*     (2006.01)
    *A46B 11/00*     (2006.01)
    *A46B 15/00*     (2006.01)
    *A46B 17/04*     (2006.01)

(52) U.S. Cl.
    CPC ........ *A46B 11/0041* (2013.01); *A46B 15/0081* (2013.01); *A46B 17/04* (2013.01); *A61B 17/244* (2013.01); *A61C 15/00* (2013.01); *A46B 2200/108* (2013.01)

(56) References Cited

U.S. PATENT DOCUMENTS

| | | | |
|---|---|---|---|
| 4,875,602 A | | 10/1989 | Chickering |
| 5,028,158 A | * | 7/1991 | Fey ................ 401/183 |
| 5,129,824 A | | 7/1992 | Keller |
| 5,829,976 A | * | 11/1998 | Green ............... 433/89 |
| 6,793,433 B2 | * | 9/2004 | Giraldo ............. 401/270 |
| 6,805,512 B2 | * | 10/2004 | King ................. 401/270 |
| 6,932,603 B2 | * | 8/2005 | Han et al. ........... 433/80 |
| 7,232,310 B2 | * | 6/2007 | Han et al. ........... 433/80 |
| 7,648,296 B2 | * | 1/2010 | Wong ............... 401/134 |
| 2004/0057773 A1 | * | 3/2004 | Gray ................ 401/277 |
| 2005/0147460 A1 | | 7/2005 | Han |
| 2005/0232687 A1 | * | 10/2005 | Zeh et al. ........... 401/269 |
| 2006/0140708 A1 | * | 6/2006 | Byun ................ 401/270 |
| 2008/0003049 A1 | | 1/2008 | Peuker |
| 2011/0013969 A1 | * | 1/2011 | Allen ............... 401/270 |
| 2012/0077145 A1 | * | 3/2012 | Tsurukawa et al. ........ 433/82 |

FOREIGN PATENT DOCUMENTS

| | | |
|---|---|---|
| JP | H5-502390 | 4/1993 |
| JP | H8-266336 | 10/1996 |
| JP | H10-113230 | 5/1998 |
| JP | 2002-234561 A1 | 8/2002 |
| JP | 3844261 B2 | 11/2006 |
| JP | 2007-501651 A1 | 2/2007 |
| JP | 2007-509821 | 4/2007 |

\* cited by examiner (a)

(b)

(a)

(b)

(a)

(b)

DRUG-CONTAINING PERSONAL HYGIENE IMPLEMENT

TECHNICAL FIELD

The present invention relates to a drug-containing personal hygiene implement to be used for implementing care of a mouth cavity, skin, skin of scalp and the like of human beings or animals.

BACKGROUND ART

Conventionally, an interdental brush has been used to remove any food debris or dental plaque and the like in a gap between teeth which cannot be removed by a normal toothbrush or to massage gum in an interdentium part (e.g., Patent Document 1 and the like). In addition, since a large number of anaerobic bacteria hide in a gap region between teeth, use of a drug when an interdental brush is used is effective, and a drug for a mouth cavity such as a dentifrice is often used by being applied to bristles when an interdental brush is used.

While such an interdental brush, however, is often used outside of home, in such a case, it is inconvenient to carry both an interdental brush and a drug bottle in terms of portability. Hence, a drug-containing interdental brush in which an interdental brush is integrally formed with a drug bottle has been developed (e.g., Patent Document 2 and the like).

CITATION LIST

Patent Literature

Patent Document 1: JP-A No. H8-266336
Patent Document 2: Japanese Patent No. 3844261

SUMMARY OF INVENTION

Technical Problem

In a conventional interdental brush of drug-containing type in the above-mentioned Patent Document 2, however, while it is convenient in that there is no need to carry both personal hygiene implement and drug bottle container, production at a plant (after a drug is contained, in particular) and subsequent product management are difficult since a drug supply aperture from a drug bottle is open. In particular, stored drug is expelled from the supply aperture when external force acts on a bottle during manufacture, and the external force similarly might act during transportation or storage after manufacture. In addition, exterior and interior of the drug bottle are in communication with each other, which thus poses a problem from the aspect of good hygiene.

Hence, an object of the present invention is to provide an economical and sanitary drug-containing personal hygiene implement that is easy to produce and manage, and has an excellent portability even when it is used as a personal hygiene implement and a drug applicator outside of home.

Solution to Problem

A drug-containing personal hygiene implement according to a first aspect of the present invention includes a bottle body in which a drug is stored, a personal hygiene body which has a shaft section and a distal-end side personal hygiene section, protrudes to a distal-end side of the bottle body, and is used to implement care of a human body, and a passage provided on a distal-end section of the bottle body and guiding the stored drug to the personal hygiene body, wherein by opening operation, the passage in the interior of the bottle body enables the drug to flow therethrough.

A drug-containing personal hygiene implement according to a second aspect is the drug-containing personal hygiene implement according to the first aspect, further including a cap body covering the personal hygiene body, wherein a passage for guiding the stored drug to a base end side of the shaft section of the personal hygiene body is provided in the distal-end section of the bottle body, a base end section of the cap body is installed consecutively with the distal-end section of the bottle body so as to block the passage, and by opening operation of twisting off the base end section of the cap body to separate it from the bottle body, a discharge opening of the passage is formed.

A drug-containing personal hygiene implement according to a third aspect is the drug-containing personal hygiene implement according to the second aspect, wherein a tubular protrusion which tubularly projects to cover the shaft section of the personal hygiene body is provided at the distal-end section of the bottle body, and a passage for guiding the drug to a distal-end side of the tubular protrusion is provided at an inner side of the tubular protrusion, and the base end section of the cap body is provided on a distal-end side of the tubular protrusion so as to block the passage.

A drug-containing personal hygiene implement according to a fourth aspect is the drug-containing personal hygiene implement according to the first aspect, wherein the bottle body has a seal section provided at a distal end of a neck section, and the drug is stored in the interior thereof in a hermetically-sealed state, the implement includes a cap member to be attached to the neck section of the bottle body, the personal hygiene body protrudes to an outer surface side of the cap member, a protrusion is provided on an inner surface side of the cap member facing the seal section of the bottle body, a through-hole for drug distribution leading from the inner surface side to the outer surface side of the cap member is provided, and by opening operation of attaching the cap member to the neck section of the bottle body, the protrusion penetrates the seal section, thereby making it possible to supply the drug in the interior of the bottle body to a periphery of a base end section of the personal hygiene body via the through-hole.

A drug-containing personal hygiene implement according to a fifth aspect is the drug-containing personal hygiene implement according to the fourth aspect, wherein a tubular protrusion which tubularly projects to the outer surface side of the cap member is provided, the personal hygiene body is protruded on the inner side of the tubular protrusion, the through-hole is opened similarly in the interior of the tubular protrusion, and the inner side of the tubular protrusion is formed as a trap section for the drug.

A drug-containing personal hygiene implement according to a sixth aspect is the drug-containing personal hygiene implement according to the fourth aspect or fifth aspect, wherein the through-hole leads from the protrusion of the cap member to the outer surface side of the cap member.

A drug-containing personal hygiene implement according to a seventh aspect is the drug-containing personal hygiene implement according to any of the second aspect to the sixth aspect, wherein the personal hygiene body is an interdental brush body in which the personal hygiene section is an interdental brush section, a toothbrush body in which the personal hygiene section is a toothbrush section, or a tongue cleaner body in which the personal hygiene section is a tongue cleaner section, and wherein the drug is supplied to the personal hygiene section along the outer surface of the shaft section.

A drug-containing personal hygiene implement according to an eighth aspect is the drug-containing personal hygiene implement according to the first aspect, wherein the bottle body has a seal section provided at a distal end of a neck section, and the drug is stored in the interior thereof in a hermetically-sealed state, the personal hygiene body has a flow passageway through which the drug axially flows to the interior of the shaft section and has a discharge opening for discharging the drug to the personal hygiene section, the implement includes a cap member attached to the neck section of the bottle body, the personal hygiene body protrudes to the outer surface side of the cap member, a protrusion is provided on the inner surface side of the cap member facing the seal section of the bottle body, a through-hole for drug distribution in communication with the flow passageway of the shaft section of the personal hygiene body protruding from the protrusion of the cap member to the outer surface side is provided, and by opening operation of attaching the cap member to the neck section of the bottle body, the protrusion penetrates the seal section, thereby making it possible to supply the drug in the bottle body to the flow passageway of the shaft section of the personal hygiene body via the through-hole.

A drug-containing personal hygiene implement according to a ninth aspect is the drug-containing personal hygiene implement according to the first aspect, further including a cap body for air-tightly covering the personal hygiene body in a space with the distal-end section of the bottle body, wherein the personal hygiene body has a flow passageway through which the drug axially flows to the interior of the shaft section, and has a discharge opening for discharging the drug to the personal hygiene section, a passage which communicates to the flow passageway of the shaft section of the personal hygiene body and guides the stored drug to the flow passageway is provided at the distal-end section of the bottle body, and by opening operation of twisting off a base end section of the cap body to separate it from the bottle body, the drug in the interior of the bottle body can be supplied to the flow passageway of the shaft section of the personal hygiene body through the passage.

A drug-containing personal hygiene implement according to a tenth aspect is the drug-containing personal hygiene implement according to the ninth aspect, wherein a slit valve is provided in the passage at the distal-end section of the bottle body.

A drug-containing personal hygiene implement according to an eleventh aspect is the drug-containing personal hygiene implement according to any of the eighth aspect to the tenth aspect, wherein the personal hygiene body is an interdental brush body in which the personal hygiene section is an interdental brush section, a toothbrush body in which the personal hygiene section is a toothbrush section, a tongue cleaner body in which the personal hygiene section is a tongue cleaner section, a toothpick body in which the personal hygiene section is a tapered drug discharge section, a tooth surface cleaning body in which the personal hygiene body is a tooth surface cleaning section, or a drug application body in which the personal hygiene body is a drug application section, and wherein the drug is supplied to the personal hygiene section through the flow passageway in the interior of the shaft section and discharged from the discharging opening.

A drug-containing personal hygiene implement according to a twelfth aspect is the drug-containing personal hygiene implement according to any of the first aspect to the eleventh aspect, wherein the bottle body is composed of soft resin.

A drug-containing personal hygiene implement according to a thirteenth aspect is the drug-containing personal hygiene implement according to the twelfth aspect, wherein the soft resin contains low-density polyethylene (LDPE).

A drug-containing personal hygiene implement according to a fourteenth aspect is the drug-containing personal hygiene implement according to any of the first aspect to the thirteenth aspect, wherein the bottle body is molded by a blow-fill-seal method.

A drug-containing personal hygiene implement according to a fifteenth aspect is the drug-containing personal hygiene implement according to any of the first aspect to the fourteenth aspect, the implement is provided with a holder having a holder main body section capable of storing the bottle body and composed of hard material and a holder cap section covering the personal hygiene body and similarly composed of hard material, the holder main body section has an opening, through which the bottle body to be stored can be pressed with fingers from the side, provided on a surrounding wall, and the holder cap section is detachably provided at a distal-end section of the holder main body section.

A drug-containing personal hygiene implement according to a sixteenth aspect is the drug-containing personal hygiene implement according to any of the first aspect to the fourteenth aspect, wherein the implement is provided with a holder having a holder main body section capable of storing the bottle body and composed of hard material and a holder cap section covering the personal hygiene body and similarly composed of hard material, the holder main body section is provided with a pressing mechanism which presses and compresses the bottle body to be stored from the base end side with a pressing member, and the holder cap section is detachably provided at the distal-end section of the holder main body section.

A drug-containing personal hygiene implement according to a seventeenth aspect is the drug-containing personal hygiene implement according to the sixteenth aspect, wherein the pressing mechanism comprises a screw rod built in the base end side of the holder main body section, the pressing member threaded onto the screw rod and mounted to be not rotatable to the inner wall of the holder main body section and movable to an axial direction, and an operating member for rotating and operating the screw rod.

A drug-containing personal hygiene implement according to an eighteenth aspect is the drug-containing personal hygiene implement according to the sixteenth aspect or the seventeenth aspect, wherein the bottle body is configured to be in a bellows shape which can be freely compressed or deformed in the axial direction.

Advantageous Effects of Invention

With a drug-containing personal hygiene implement according to a first aspect, since a personal hygiene implement and a drug are integrated, thus portability and convenience being excellent, and a configuration is such that by opening operation, the drug can flow in a passage inside a bottle body and is supplied to a personal hygiene body, there is no risk that after the drug is sealed, even if unforeseeable external force acts on the bottle body during manufacture or during management such as transportation, storage and the like, thus making the manufacturing and management easy. In addition, since the drug is sealed in the bottle body before the opening operation, the drug-containing personal hygiene implement being excellent in terms of hygiene can be provided.

With a drug-containing personal hygiene implement according to a second aspect, since the implement further includes a cap body covering the personal hygiene body, a passage for guiding stored drug to a base end side of the shaft section of the personal hygiene body is provided at a distal-end section of the bottle body, the base end of the cap body is installed consecutively with the distal-end section of the bottle body so as to block the passage, and a discharge opening of the passage is formed by opening operation of twisting off the base end section of the cap body to separate it from the bottle body, therefore, the personal hygiene body is covered by the cap body and thus the implement is preferable in terms of hygiene. In addition, since the passage is opened in conjunction with operation of removing the cap at the point of use, the drug-containing personal hygiene implement with excellent operability can be provided.

With a drug-containing personal hygiene implement according to a third aspect, since a tubular protrusion which tubularly projects to cover the shaft section of the personal hygiene body is provided at the distal-end section of the bottle body, a passage for guiding the drug to the distal-end side of the tubular protrusion is provided at an inner side of the tubular protrusion, and the base end section of the cap body is provided at the distal-end side of the tubular protrusion so as to block the passage, therefore, dripping of the drug during use can be prevented, and the drug can be efficiently supplied to the personal hygiene body without splattering even if a large amount of the drug is discharged.

With a drug-containing personal hygiene implement according to a fourth aspect, since a personal hygiene body and cap member can be configured separately from a bottle body, for example, only a bottle body in which a drug has been used up can be replaced with a new one, and the personal hygiene body and cap member can be reused, which is convenient for users. In addition, in terms of manufacturing, since the personal hygiene body and cap member can be manufactured and managed separately from the bottle body, efficient manufacturing is possible.

With a drug-containing personal hygiene implement according to a fifth aspect, since a tubular protrusion which tubularly projects is provided at the outer surface side of the cap member, the personal hygiene body protrudes to the inner side of the tubular protrusion, the through-hole is opened similarly on the inner side of the tubular protrusion, and the inner side of the tubular protrusion is formed as a trap section for the drug, therefore, dripping of the drug can be prevented more reliably, and the drug can be efficiently supplied to the personal hygiene body without splattering even if a large amount of the drug is discharged.

With a drug-containing personal hygiene implement according to a sixth aspect, since a through-hole is provided to lead from a protrusion of a cap member to an outer surface side of the cap member, a drug inside a bottle can be reliably supplied to a personal hygiene body via the through-hole of the protrusion which penetrates a seal section of a bottle body. In addition, an amount of drug supply can be easily adjusted by opening or closing of the cap member.

With a drug-containing personal hygiene implement according to a seventh aspect, the implement can be carried away from home, and conveniently used while applying a drug as an interdental brush, toothbrush, or tongue cleaner.

With a drug-containing personal hygiene implement according to an eighth aspect, since a personal hygiene body and cap body can be configured separately from a bottle body, as with the drug-containing personal hygiene implement according to the fourth aspect, only a bottle body in which a drug has been used up can be replaced with a new one, and the personal hygiene body and cap member can be reused, which is convenient for users. In addition, in terms of manufacturing, since the personal hygiene body and cap member can be manufactured and managed separately from the bottle body, efficient manufacturing is possible. In addition, the personal hygiene body has a flow passageway through which a drug is flowed axially inside a shaft section, and has a discharge opening through which the drug is discharged to a personal hygiene body. Hence, when a protrusion penetrates a seal section by opening operation, the drug is supplied to the flow passageway of the shaft section of the personal hygiene body via the through-hole, thus making it possible to supply the drug to the personal hygiene body more reliably.

With a drug-containing personal hygiene implement according to a ninth aspect, since the implement further includes a cap body for air-tightly covering a personal hygiene body in a space with a distal-end section of the bottle body, the implement is favorable in terms of hygiene. In addition, since a passage is opened in conjunction with operation of removing a cap at the point of use, the drug-containing personal hygiene implement with excellent operability can be provided. In addition, rather than consecutively installing a base end of the cap body with a distal-end section of the bottle body so as to block the passage, simply by air-tightly covering the personal hygiene body in a space with the distal-end section of the bottle body, the implement is configured to prevent a drug from being discharged not by physically blocking the flow passageway but by making the air-tight covering. Hence, the structure is simplified and degree of freedom of designing improves, thereby making it possible to reduce manufacturing costs.

With a drug-containing personal hygiene implement according to a tenth aspect, since a slit valve is provided in a passage of a distal-end section of a bottle body, leakage of a drug to a cap side can be prevented even if the bottle body is pressed with unforeseeable great power. In addition, even after opening, excessive discharge of the drug can also be controlled even if the bottle body is strongly pressed.

With a drug-containing personal hygiene implement according to an eleventh aspect, as a structure capable of sharing a drug through a flow passageway inside a shaft section, the implement can be carried away from home, and conveniently used while applying a drug as an interdental brush body, toothbrush body, tongue cleaner body, toothpick body, tooth surface cleaning body, and drug application body.

With a drug-containing personal hygiene implement according to a twelfth aspect, since a bottle body is composed of soft resin, an appropriate amount of drug can be easily squeezed by pressing the bottle body with a hand, without any need for a special structure.

With a drug-containing personal hygiene implement according to a thirteenth aspect, since soft resin contains low-density polyethylene (LDPE), a light weight bottle body with excellent operability can be obtained.

With a drug-containing personal hygiene implement according to a fourteenth aspect, since a bottle body is molded by means of a blow-fill-seal method, a bottle can be filled with a drug in a sterile environment, and the drug can be stored for a long term without a need of blending preservatives such as paraben and alcohol.

With a drug-containing personal hygiene implement according to a fifteenth aspect, since a holder which has a holder main body section capable of storing a bottle body and composed of a hard material, and a holder cap section covering the personal hygiene body and made similarly of a hard material is provided, the personal hygiene implement can be protected (protected against any physical external force as well as in terms of hygiene) while it is carried. In addition, the holder featuring a design by making a structure of a personal hygiene body or the bottle body invisible can make a product with excellent appearance, increase added value of the product, and improve easiness to hold during use. In addition, an unanticipated situation can be prevented in which a bottle body is pressed in a bag and the like and a drug is discharged into the bag and the like while a once opened and used personal hygiene implement is carried. Since the holder main body section has an opening, through which the bottle body to be stored can be pressed with fingers from the side, provided on a surrounding wall, the bottle body can be pressed with a finger while the holder is mounted, thereby making it possible to easily squeeze the drug.

With a drug-containing personal hygiene implement according to a sixteenth aspect, provision of a pressing mechanism which compresses a bottle body to be stored in a holder main body section by pressing it with a pressing member from a base end side enables a drug to be easily squeezed.

With a drug-containing personal hygiene implement according to a seventeenth aspect, an appropriate amount of drug can be squeezed as intended by rotating an operating member, as necessary, and adjusting an amount of the drug to be discharged.

With a drug-containing personal hygiene implement according to an eighteenth aspect, since a bottle body has a bellows shape, a drug can be easily squeezed to the end even when the bottle body is filled with a relatively viscous drug.

BRIEF DESCRIPTION OF THE DRAWINGS

FIG. 1(a) is a side elevation showing a state before opening whereby a cap body is removed. FIG. 1(b) is a side elevation showing a state after the opening in which the cap body has been removed.

Figure 1:
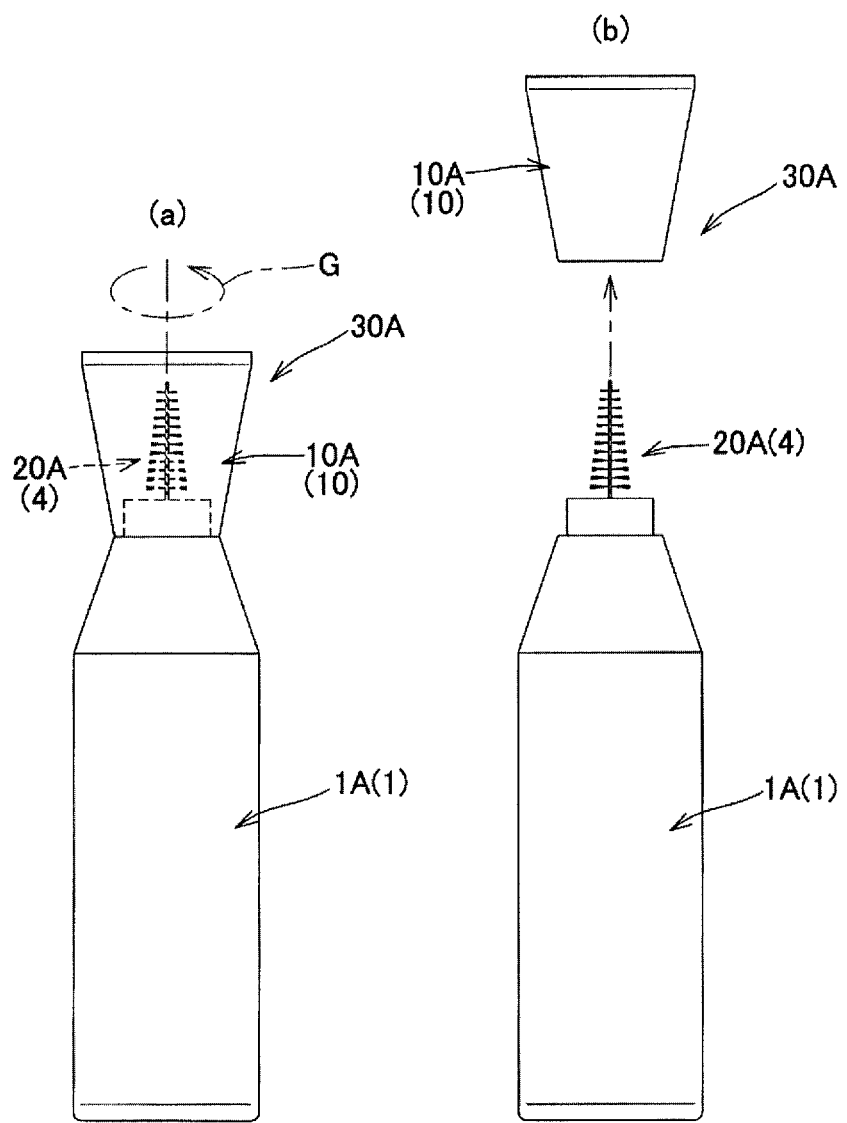
FIG. 1 is an overall configuration diagram of a drug-containing personal hygiene implement according to a first embodiment of the present invention.

REFERENCE SIGNS LIST 1A, 1C, 1E Bottle body
2 Drug
4 Personal hygiene body
5 Shaft section
6 Personal hygiene section
10A to 10E Cap body
13 Brush supporting section
14, 14A to 14E Passage
15a Opening
15b Discharge opening
16 Tubular protrusion
17 Trap section
18 Connecting plate
19 Embedded section
20, 20A, 20B Interdental brush body
20C Tongue cleaner body
21, 21A Brush shaft section
21a to 21d Base end section
22, 22A Brush section
23, 24 Concave groove
25 Die parting line
26, 26A Interdental brush section
26B Toothbrush section
26C Tongue cleaner section
30, 30A to 30E Drug-containing personal hygiene implement
35 Die parting line
41A, 41B Bottle body
43A, 43B Main body section
44 Neck section
45 Seal section
46 Screw section
47 Engaged section
50 Pressing mechanism
51 Abutting section
52 Connecting section
53 Bottom
54 Screw hole
55 Guiding section
56, 57 Engaged concave section
58, 59 Engaged section
60A Neck section
60A, 60B Cap member
61 Inner surface
62 Outer surface
63A, 63B Protrusion
64A Passage
65a, 65b Opening
66 Upper wall section
67 Tubular protrusion
68 Female screw section
69 Embedded section
71 Brush shaft section
72 Brush section
73a to 73d Base end section
75 Trap section
80 Holder
81 Holder main body section
82 Holder cap section
83 Opening
84 Annular convex section
85 Annular concave groove
90 Holder
91 Holder main body section
92 Holder cap section
93 Annular convex section 95 Operating section
96 Screw rod
97 Pressing member
98, 99 Engaged section
100A, 100B Drug-containing personal hygiene implement
143 Bottle body
160 Cap member
162 Through-hole
164 Brush hair
165, 175 Flow passageway
170 Interdental brush body
171 Interdental brush section
172 Brush shaft section
176 Discharge path
178 Brush strip
200 Drug-containing personal hygiene implement
260 Toothbrush body
261 Toothbrush section
263 Head
264 Brush hair
265, 275, 285, 295 Flow passageway
266 Discharge path
270, 280, 290, 300 Tongue cleaner body
271, 281, 291, 301 Tongue cleaner section
276 Discharge opening
294 Brush hair
296 Discharge opening
304 Brush hair
306 Discharge opening
310, 320, 330, 340 Tooth surface cleaning body
311, 321, 331, 341 Tooth surface cleaning section
315, 325, 335, 345, 355, 365, 371, 375 Flow passageway
316, 326 Discharge opening
350 Toothpick body 356 Drug discharge section
360, 370, 380, 390, 400, 410 Drug application body
361, 371, 381, 391, 401, 411 Drug application section
395 Through-bore
396 Discharge opening
411 Ball
415 Flow passageway
419 Retainer
500 Drug-containing personal hygiene implement
501 Bottle body
510 Cap body
520 Slit valve
521 Opening/closing slit
522 Valve retaining member

DESCRIPTION OF EMBODIMENT

A drug-containing personal hygiene implement of the present invention is characterized in that the implement includes a bottle body in which a drug is stored, a personal hygiene body which has a shaft section and a distal-end personal hygiene section, protrudes onto a distal end side of the bottle body, and is used to implement care of a mouth cavity, skin, skin of scalp and the like of human beings or animals, and a passage which is provided at the distal end of the bottle body and guides the stored drug to the personal hygiene body, and that opening operation makes it possible for the drug to flow through the passage inside the bottle body. FIG. 1 to FIG. 13 show a first embodiment, FIG. 14 to FIG. 25 a second embodiment, FIG. 26 to FIG. 36 a third embodiment, and FIGS. 37 and 38 a fourth embodiment.

First, the first embodiment of the present invention will be described based on FIG. 1 to FIG. 13.

As shown in FIG. 1, a drug-containing personal hygiene implement 30A of the embodiment includes a bottle body 1A in which a drug is stored, an interdental brush body 20A which is a personal hygiene body 4 protruding from a distal end section of the bottle body 1A in a shaft line direction, and a cap body 10A attached to a distal end of the bottle body 1A and covering the interdental brush body 20A, the implement having a structure that enables the drug to be discharged by opening operation of twisting off a base end section of the cap body 10A to separate it from the bottle body 1A.

The drug-containing personal hygiene implement 30A is manufactured by a sterile filling and packaging manufacturing machine in a series of blow-fill-seal (BFS) processes. The blow-fill-seal process is a manufacturing process in which a sterile drug is sealed in a sterile container in a sterile environment. Thus, the drug in the bottle body 1A can be stored for a long term without blending preservatives such as paraben, alcohol and the like. By making size of the bottle body 1A smaller and capacity of the drug to be filled an amount equivalent to one-time dosage, the implement can be a disposable type for one-time use which is small-size and has excellent portability.

The bottle body 1A is a part which contains a drug in its interior and to which a user puts his/her fingers and holds with his/her hands during use. The bottle body 1A is made from soft polyethylene such as low-density polyethylene (LDPE) and the like, soft thermoplastic synthetic resin such as polypropylene (PP), ethylene-vinyl acetate copolymer (EVA), EVOH, or nylon, alone or as a polymer blend, and can be single-layered or multi-layered. Composed of soft resin, such a bottle body 1A can be structured such that the drug can be easily squeezed by pressing the bottle body 1A with fingers. Composed of low-density polyethylene (LDPE), in particular, the bottle body 1A can be made light-weight and have excellent operability.

A drug to be stored in the bottle body 1A may be selected as appropriate, depending on a type of a personal hygiene body 4. If the personal hygiene body 4 is an interdental brush body 20A, as in this case, the drug is selected in accordance with a purpose such as prevention and treatment of periodontal disease, prevention of dental caries, whitening, moisture retention, treatment and the like. For example, a liquid or gel composition having flow property such as an interdental gel, mouthwash, gel dentifrice, interdental coating agent and the like can be used.

Figure 2:
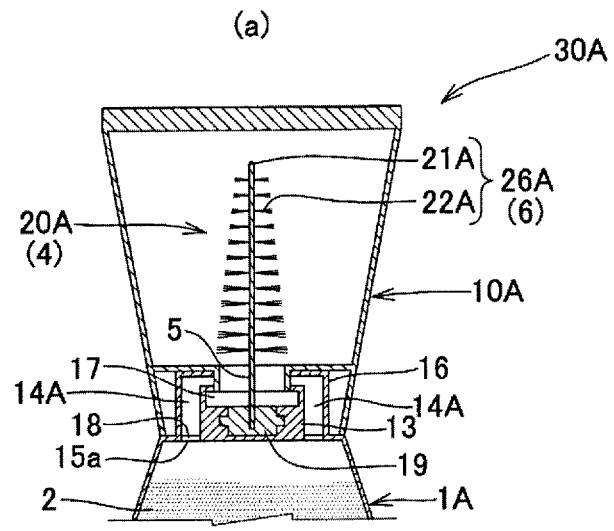
FIG. 2(a) is a vertical cross-sectional view showing a main part of the same drug-containing personal hygiene implement before opening.
FIG. 2(b) shows a vertical cross-sectional view showing the same main part after opening.
FIG. 2(c) is a transverse cross-sectional view of A-A of FIG. 2(b).
Figure 2:
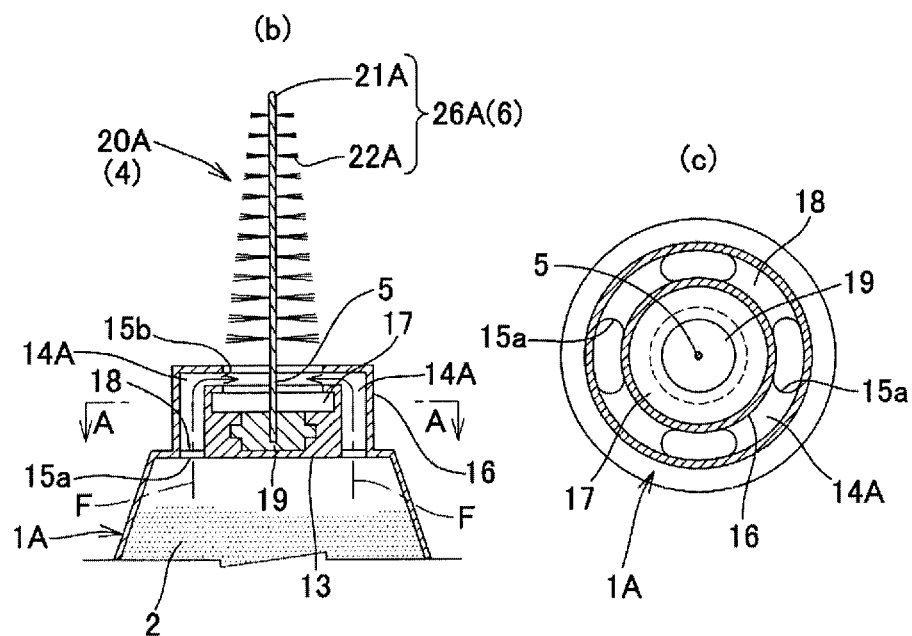
Figure 3:
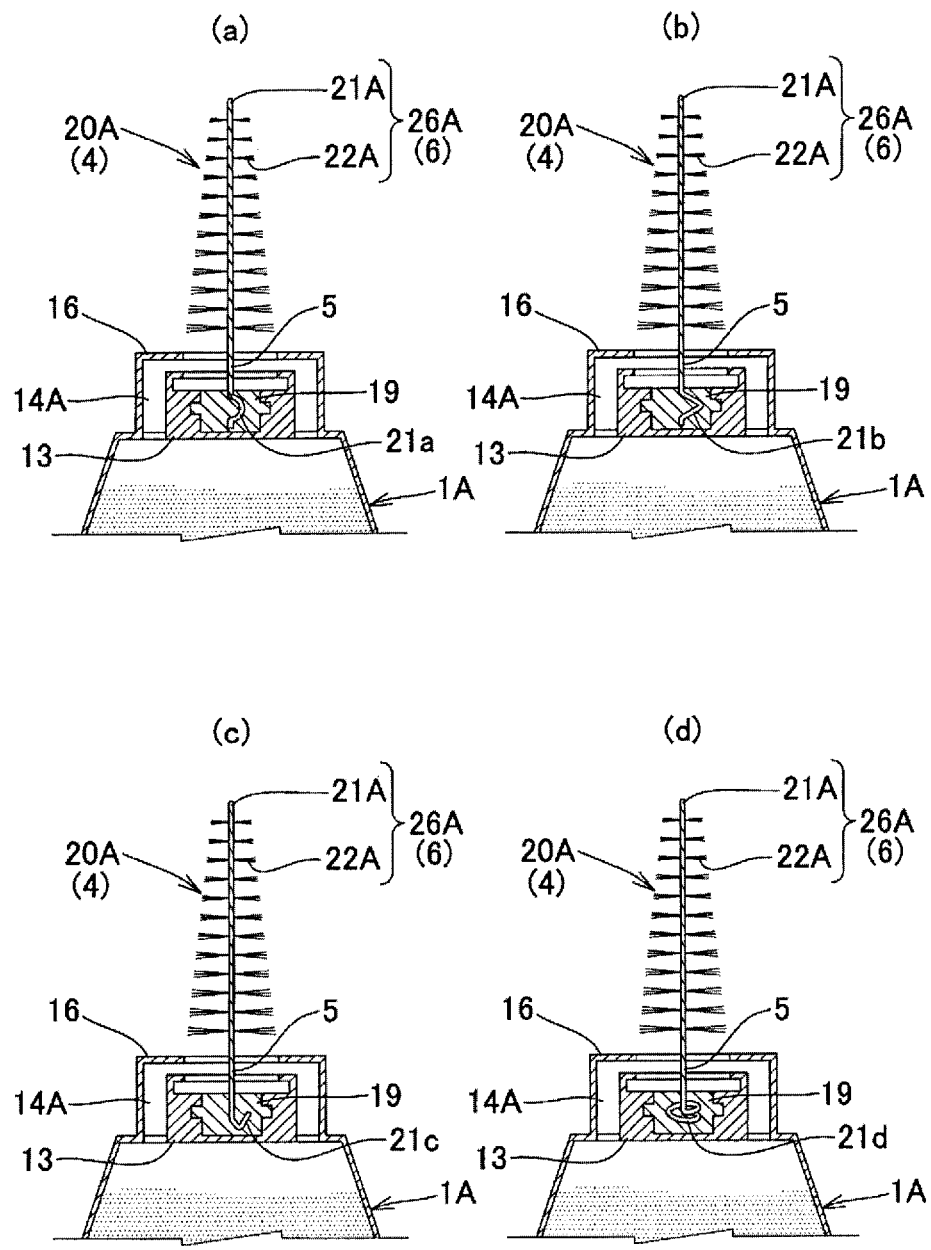
FIGS. 3(a) to (d) are cross-sectional views showing variants of a shaft section of the same drug-containing personal hygiene implement.

At the distal end section of the bottle body 1A are provided a brush supporting section 13 in which a shaft section 5 of the interdental brush body 20A, which is the personal hygiene body 4, is embedded and supported, and a tubular protrusion 16 provided in an outer periphery of the brush supporting section, as shown in FIG. 2. The tubular protrusion 16 is the tubular protrusion 16 which tubularly projects to the outer periphery of the brush supporting section 13 so that it covers the shaft section 5 on the base end side of the interdental brush body 20A, which is the personal hygiene body 4 supported by the brush supporting section 13 and protruding at the distal end side. On the inner side of the wall (interior of wall) of the tubular protrusion 16 is provided a passage 14A for guiding the drug 2 to the distal end of the tubular protrusion 16.

In addition, a connecting plate 18 is provided on the inner surface side of the distal end section of the bottle body 1A. The connecting plate 18 is provided on the bottom of the tubular protrusion 16, and a base-end side outer peripheral surface of the brush supporting section 13 is connected to the distal-end outer periphery of the bottle body 1A and supported by the connecting plate 18. As shown in FIG. 2(c), multiple openings 15a are circumferentially formed at given intervals on the connecting plate 18 and function as openings 15a on the bottle body side of the passage 14A which is on the inner side of the wall of the tubular protrusion 16. The tubular protrusion 16 and passage 14A in the inner side of the wall thereof are curved to the shaft center direction on the distal end side. A discharge opening 15b of the passage 14A is positioned on an inner peripheral surface facing the base end section of the interdental brush body 20A which is the personal hygiene body 4 at the distal end of the inflected tubular protrusion 16, and is blocked by the base end section of the cap body 10A before opening. Then, by opening operation of removing the cap body 10A, the discharge opening 15b opens, and, as shown in FIG. 2(b), the drug 2 flows through the passage 14 in a direction shown by arrow F and is discharged onto the brush supporting section 13 inside the tubular protrusion 16.

A concave space of the upper part of the brush supporting section 13, which is the inner side of the tubular protrusion 16, serves as a trap section 17 for the drug 2. The trap section 17 can not only prevent dripping of the drug 2 applied to the interdental brush body 20A, which is the personal hygiene body 4, but also prevent the drug from splattering, thereby enabling efficient supply to the interdental brush body 20. If the drug 2 has low viscosity, by once stopping at the trap section 17, the drug 2 moves along the shaft section 5, being supplied to brush sections 22 of the interdental brush body 20A. Capillary phenomenon occurs, the drug 2 gradually infiltrates to an upper part of a brush shaft section 21, and adheres to the brush sections 22. On the other hand, if the drug 2 has high viscosity, it can be directly applied to the brush sections 22.

After filling of the drug 2, the base end section of the cap body 10A is fixed to the inner peripheral surface of a curved part at the distal end of the tubular protrusion 16 so as to block the discharge opening 15b. Specifically, the base end section of the cap body 10A is welded by providing a joint surface on the inner peripheral surface of the curved part at the distal end of the tubular protrusion 16, so as to block the passage 14A. A joint part of the distal end of the bottle body 1A and cap body 10A is thin. When the cap body 10A is opened, the joint part is broken by forcibly rotating the cap body 10A in a direction of arrow G, as shown in FIG. 1(a), and the discharge opening 15b of the passage 14A opens, as shown in FIG. 1(b). Note that it is a preferable example that the cap body 10A is made reusable as a cap covering the personal hygiene body 4 even after being twisted off.

The interdental brush body 20A in this example, which is the personal hygiene body 4, includes a personal hygiene section 6, which is a well-known interdental brush body 26A, and a shaft section 5, the personal hygiene section 6 including the brush sections 22A wherein multiple filaments are radially implanted on the brush shaft section 21A composed of a fine metallic wire in a length direction thereof. The brush sections 22A are made, by bending the fine metallic wire double, arranging filaments orthogonally therebetween, twisting the metallic wire, radially implanting the filaments to the brush shaft section 21A composed of the metallic wire, and then cutting the filaments to desired length. For example, thermoplastic synthetic resin such as polyamide or polybuthylene terephthalate is used for the filaments. An outline of the brush section 22A may be shaped like a truncated cone, as shown in FIG. 2, or a cylinder or barrel whose outer diameter is larger at a middle part of its length than at both ends. In addition, size of the brush section 22A may be changed as appropriate. It is also possible to adopt brush sections 22A which are integrally formed by radially molding filaments made from synthetic resin or synthetic rubber on the brush shaft section 21A made from synthetic resin or metal coated with synthetic resin.

The shaft section 5 of the interdental brush body 20A continuing to the base end side of the brush shaft section 21A is buried in and supported by the brush supporting section 13 at the distal end of the bottle body 1A. Specifically, the shaft section 5 is supported by embedded section 19 buried in the brush supporting section 13. In other words, with the base end section buried inside the embedded section 19, the interdental brush body 20 is fixed to the brush supporting section 13 of the bottle body 1A. More specifically, the interdental brush body 20A is integrally molded by inserting into the brush supporting section 13 the embedded section 19 in which the shaft section 5 of the interdental brush body 20A is buried. The embedded section 19 is formed of synthetic resin harder than a material of the bottle body 1A. Specifically, hard synthetic resin such as PP, acrylonitrile styrene copolymer (AS), acrylonitrile butadiene styrene copolymer (ABS), polyethylene terephthalate (PET) and the like, is used.

As shown in the example of FIG. 2, when the base end section of the shaft section 5 to be buried in and supported by the embedded section 19 is straight, it is possible that the interdental brush body 20A may come out of the embedded section 19, depending on extreme use. Thus, in order to obviate such coming out, the base end section of the shaft section 5 may be curved and deformed, as shown in FIG. 3(a) to FIG. 3(d), for example. FIG. 3(a) is an example in which the base end section 21a of the shaft section 5 is bent in a semicircular manner. FIG. 3(b) is an example in which the base end section 21b is similarly bent in a dogleg manner. In addition, FIG. 3(c) is an example in which the base end section 21c is similarly bent like letter J (into a hook). FIG. 3(d) is an example in which the base end section 21d is similarly bent in a spiral manner.

FIG. 4 to FIG. 7 show a variant of a structure of a distal end section of the bottle body. The variant shown in FIG. 4(a) to FIG. 4(c) is a configuration example in which the distal-end side of the tubular protrusion 16 is configured to be straight, rather than making it curve inward. The distal-end section, which serves as the discharge opening 15b of the passage 14B in the inner side of the wall, is configured such that the inner wall is made shorter than the outer wall with the passage 14b sandwiched therebetween, thus directing the drug 2, after opening, to be discharged from the discharge opening 15b to the inner side above the brush supporting section 13. In a state before opening, the discharge opening 15b is blocked by the curved section of the base end section of the cap body 10B. The trap section 17 is formed on the upper part of the brush supporting section 13 inside the passage 14B.

A variant shown in FIG. 5(a) to FIG. 5(c) includes at a distal end of a bottle body 1C a tubular protrusion 16 projecting tubularly so as to cover a shaft section 5 of an interdental brush body 20A, which is a personal hygiene body 4, and a passage 14C for guiding a drug 2 to a distal-end side of the tubular protrusion 16 is provided not in the inner side of the wall of the tubular protrusion 16, but in a gap between the wall and an outer peripheral surface of an inner brush supporting section 13. The passage 14C in this example is straight and formed in the brush supporting section 13 of the bottle body 1C, and a discharge section of the passage 14C is blocked by a curved section of a base end section of a cap body 10C. In addition, a trap section 17 is formed above the brush supporting section 13, and a discharge opening 15b of the passage 14C is positioned on a bottom of the trap section 17.

Figure 4:
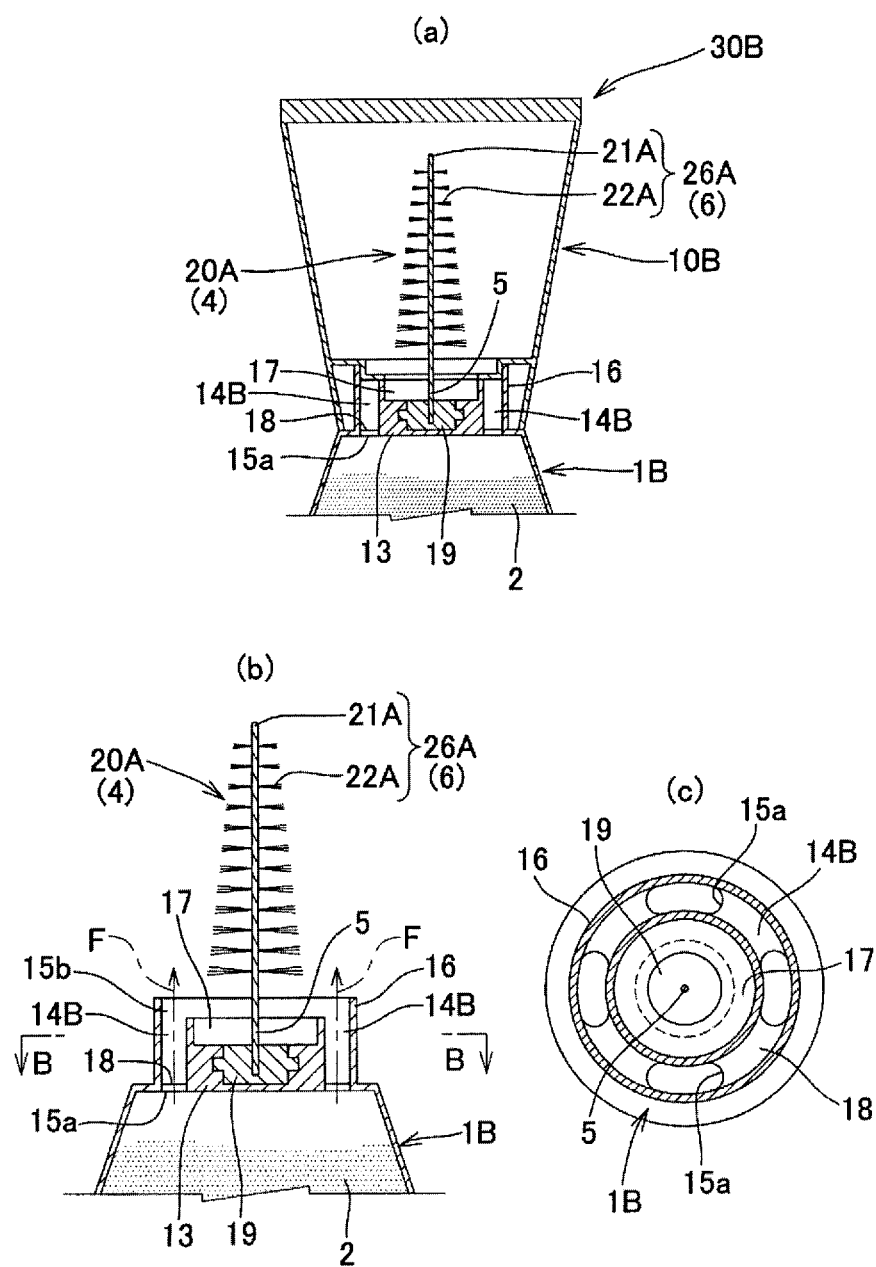
FIG. 4(a) is a vertical cross-sectional view showing a main part of a variant of a top end of a bottle body of the same drug-containing personal hygiene implement before opening.
FIG. 4(b) is a vertical cross-sectional view showing the same main part after opening.
FIG. 4(c) is a transverse cross-sectional view of B-B of FIG. 4(b).
Figure 5:
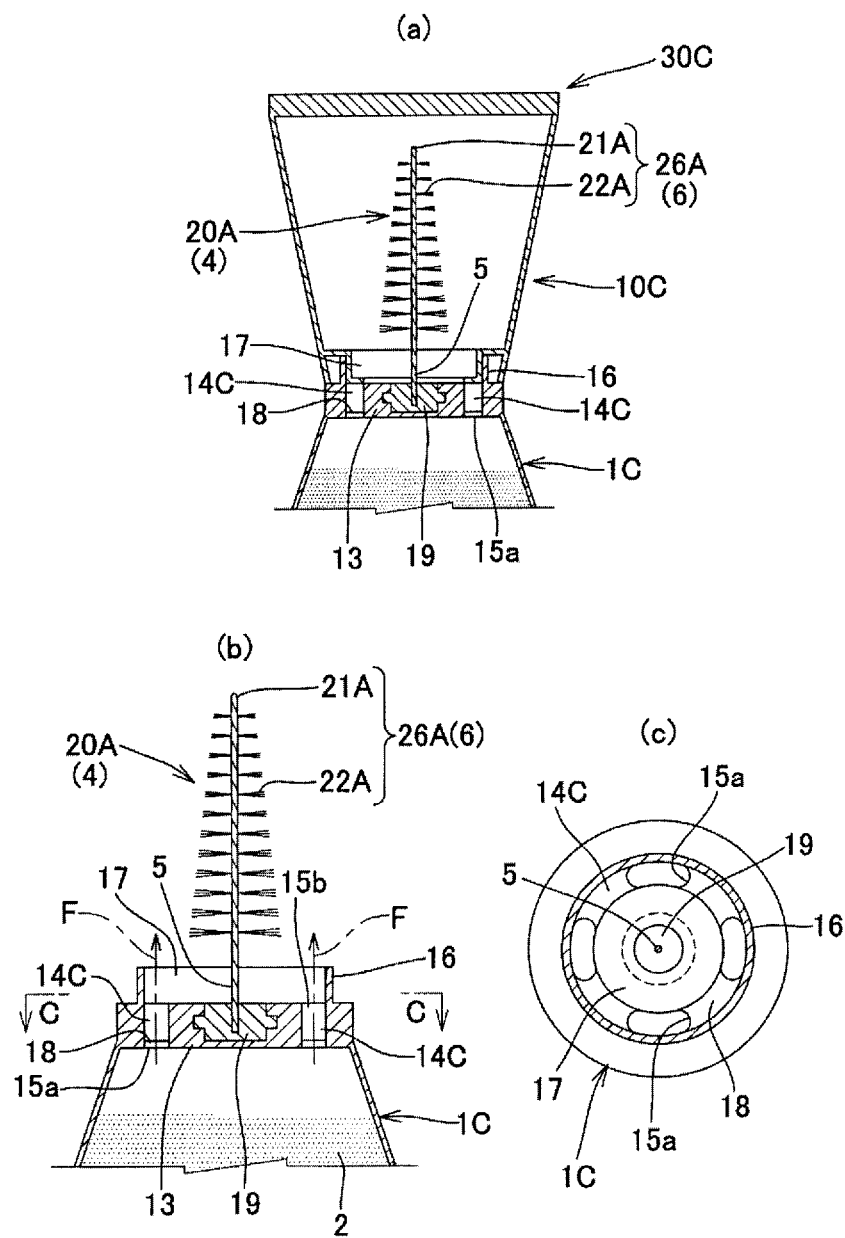
FIG. 5(a) is a vertical cross-sectional view showing a main part of other variant of a top end structure of a bottle body of the same drug-containing personal hygiene implement before opening.
FIG. 5(b) is a vertical cross-sectional view showing the same main part after opening.
FIG. 5(c) is a transverse cross-sectional view of C-C of FIG. 5(b).
Figure 6:
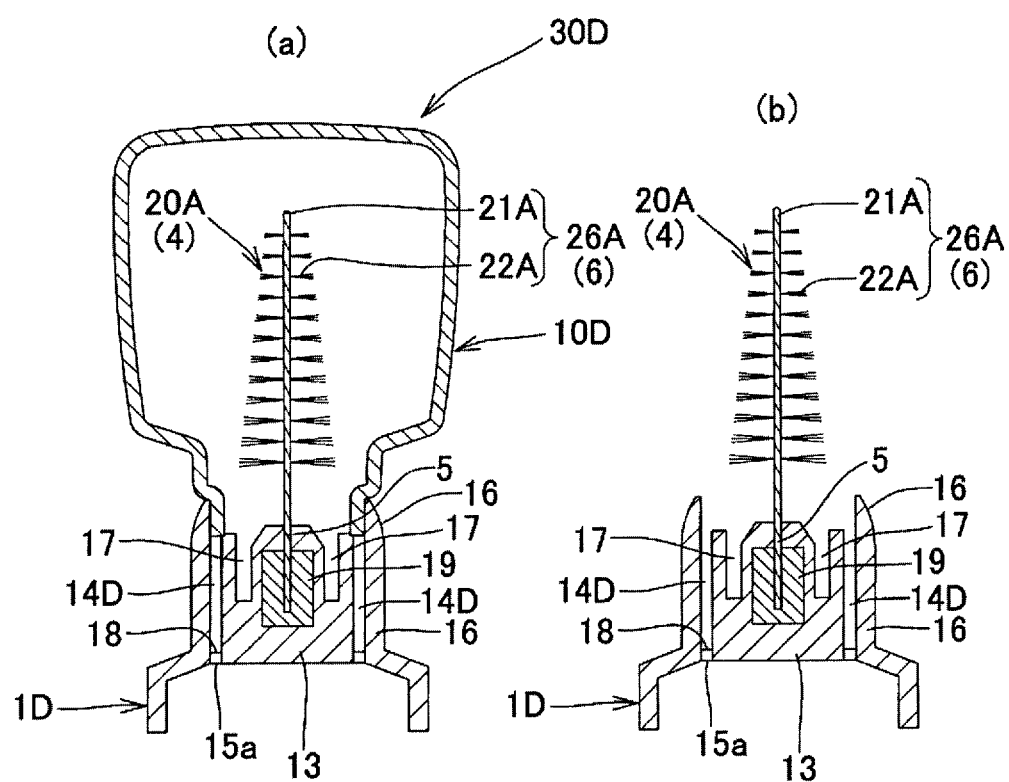
FIG. 6(a) is a vertical cross-sectional view showing a main part of yet other variant of a top end of a bottle body of the same drug-containing personal hygiene implement before opening.
FIG. 6(b) is a vertical cross-sectional view showing the same main part after opening.
Figure 7:
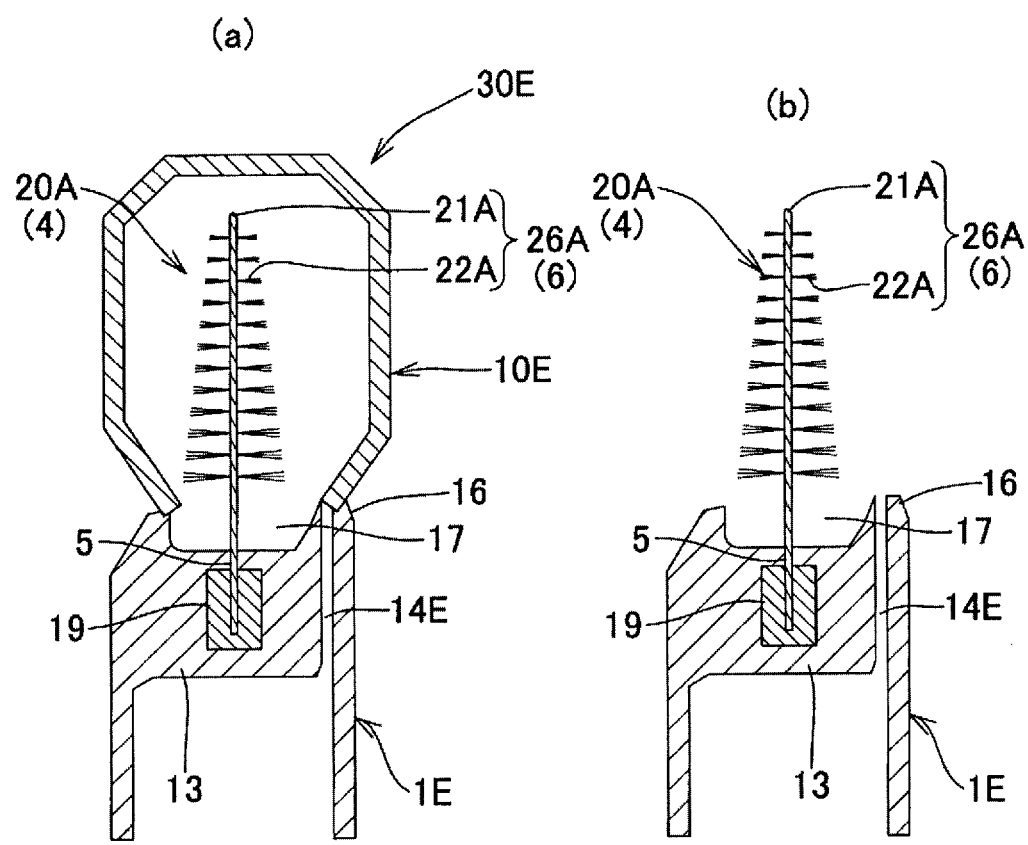
FIG. 7(a) is a vertical cross-sectional view showing a main part of even other variant of a top end of a bottle body of the same drug-containing personal hygiene implement before opening.
FIG. 7(b) is a vertical cross-sectional view showing the same main part after opening.

Similar to the example shown in FIG. 4, a variant shown in FIG. 6(a) and FIG. 6(b) is configured such that a tubular protrusion 16 is straight, and an inner wall is made lower than an outer wall, with a distal end, which serves as a discharge opening of a passage 14B in the inner side of a wall, sandwiched therebetween, thus directing a drug 2, after opening, to be discharged from the discharge opening to the inner side above the brush supporting section 13. However, a discharge opening is blocked, abutted by a linearly extending base end surface of a cap body 10D. In addition, the brush supporting section 13 bulges to a distal-end side, an internal embedded section 19 being long in an axial direction, and is such configured to improve supporting strength of an interdental brush body 20A, which is a personal hygiene body 4.

In a variant shown in FIG. 7(a) and FIG. 7(b), a brush supporting section 13 and tubular protrusion 16 are integrally molded with a bottle body 1E. A base end section of a shaft section 5 of an interdental brush body 20, which is a personal hygiene body 4, is buried in an embedded section 19 which is buried in the brush supporting section 13 at a distal end of the bottle body 1E. In addition, a passage 14E is straight and formed in communication with a gap between the brush supporting section 13 and an outer wall on a distal end side of the bottle body 1E, and with the inner side of a wall of the tubular protrusion 16 formed on the distal end side thereof. In addition, a trap section 17 is formed like a concave inside the tubular protrusion 16 on the side of an upper surface of the brush supporting section 13. Then, similar to the example of FIG. 6, a discharge opening at the distal end of the passage 14E is blocked, abutted by a base end surface of a cap body 10E which extends in a straight manner.

A method for manufacturing a drug-containing personal hygiene implement 30A of the embodiment will be described in the following.

A drug-containing personal hygiene implement 30A is manufactured in a publicly known blow-fill-seal (BFS) process by a sterile (aseptic) filling and packaging manufacturing machine. The blow-fill-seal process is a system for performing molding (blow)/filling (fill)/sealing (seal) in a series of works, wherein a container made from resin such as polyethylene is molded in the machine, and then continuously a liquid is filled and an opening is sealed. The blow-fill-seal process is characterized in that a sterile drug can be manufactured in a sterile container in a sterile environment. Thus, this enables long-term storage of drugs without blending preservatives such as paraben or alcohol, also making it possible to manufacture a drug-containing personal hygiene implements of disposable type with no preservative blended.

An interdental brush body 20A, which is a personal hygiene body 4, is prepared separately. The interdental brush body 20A is manufactured by an interdental brush manufacturing machine, using filaments of nylon and the like and metallic wires (or metallic wires coated with synthetic resin). If the interdental brush body 20A is made from synthetic resin, the filaments and brush shaft section 21A are manufactured by an injection molding process. In this case, it is preferable to use soft resin such as nylon and the like for filaments and hard resin such as polypropylene for a brush shaft section 21.

An embedded section 19 is molded on a base end side of a shaft section 5 of the interdental brush body 20. Specifically, a base end section of the shaft section 5 of the interdental brush body 20 is inserted into a die for the embedded section 19, the die is filled with thermoplastic synthetic resin, which is a material of the embedded section 19, and the resin is hardened. Then, the die for the embedded section 19 is opened and the embedded section 19 is removed. With this, the personal hygiene body 4 to be attached to a distal end section of a bottle body 1A is prepared.

The bottle body 1A is manufactured by blow molding. In this process, a tubular protrusion 16, a part of a brush supporting section 13, and main body of the bottle body 16 are molded. First, molten resin is extruded into the interior of the die in sterile air. A hollow, cylindrical main body section is molded, by feeding compressed air from an opening region through which the resin is extruded, and inflating the resin. The distal-end region is bound in the die during blow molding, and a part of the brush supporting section 13 and tubular protrusion 16 are molded.

When the main body section hardens, it is filled with a drug 2 by a filling nozzle. Desired viscosity of the drug 2 is selected, from the standpoints of discharging performance from a discharge opening 15b of a passage 14A, prevention of splattering of the drug 2 in a trap section 17, and promotion of capillary phenomenon in the shaft section 5 and a personal hygiene section 6. The viscosity of the drug 2 is not specifically limited, for example, as far as the drug 2 can be discharged from the passage 14A, which is a thin tube. However, in the case of an interdental brush body, viscosity whose value at 20° C., 60 seconds measured by using a rotating viscometer of type B is 2000 mPa·s or lower is preferable.

Then, the distal end of the bottle body 1A is molded by integrally molding the brush supporting section 13 and the interdental brush body 20A. Specifically, an embedded section 19 in which a brush shaft section 21 of the interdental brush body 20A is buried is inserted into a die for molding the distal-end section of the bottle body 1A, the die is filled with synthetic resin, which is a material of the brush supporting section 13 of the bottle body 1A, and the synthetic resin is hardened. After this, the die is opened and the bottle body 1A is removed. With this, the base end section of the shaft section 5 is buried in the brush supporting section 13 of the bottle body 1A, thus integrating the interdental brush body 20A and the bottle body 1A, and the bottle body 1A in which the internal brush body 20 is provided is formed. Note that the drug may be filled after the interdental brush body 20A and bottle body 1A are integrally molded.

A cap body 10A is separately manufactured with the same material as the bottle body 1A by the injection molding process. After the bottle body 1A is filled with the drug 2, a base end section of the cap body 10A is joined by thermally adhering to an inner peripheral surface of a curved section at a distal end of a tubular protrusion 16, which constitutes the discharge opening 15b, thus forming the bottle body 1A in which the drug is sealed. Note that a nitrogen purge may be performed before sealing if the drug 2 easily oxidizes.

Figure 8:
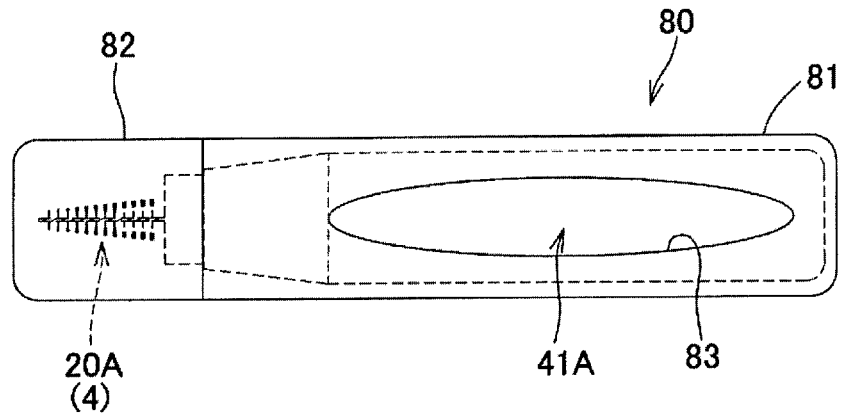
FIG. 8(a) is a side elevation showing a state in which a holder is mounted to the same drug-containing personal hygiene implement.
FIG. 8(b) is a vertical cross-sectional view of the same holder.
Figure 8:
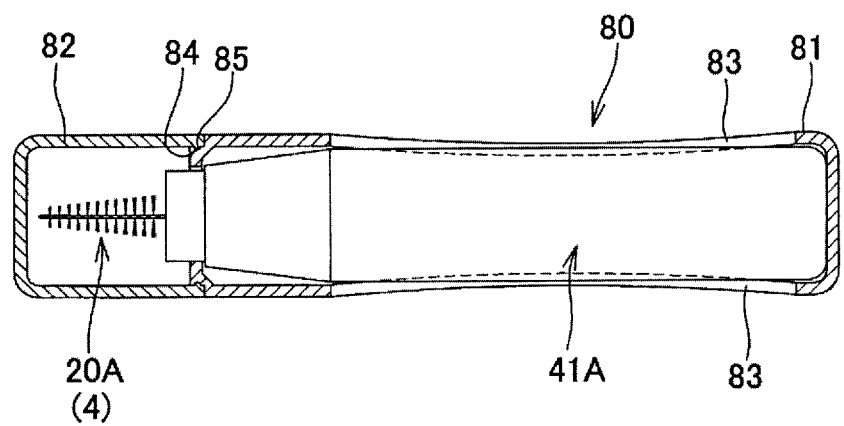

FIG. 8 shows an example of a holder to be attached to a drug-containing personal hygiene implement 30A. The holder 80 has a holder main body section 81 capable of storing a bottle body 41A, and a holder cap section 82 covering an interdental brush body 20A, which is a personal hygiene body 4. The holder 80 is made from a hard material which is harder than the bottle body 41A composed of soft resin. A hard material may be selected, as appropriate, from various hard materials, e.g., metal such as stainless or aluminum, hard synthetic resin such as polypropylene, polystyrene, and acryl.

Figure 9:
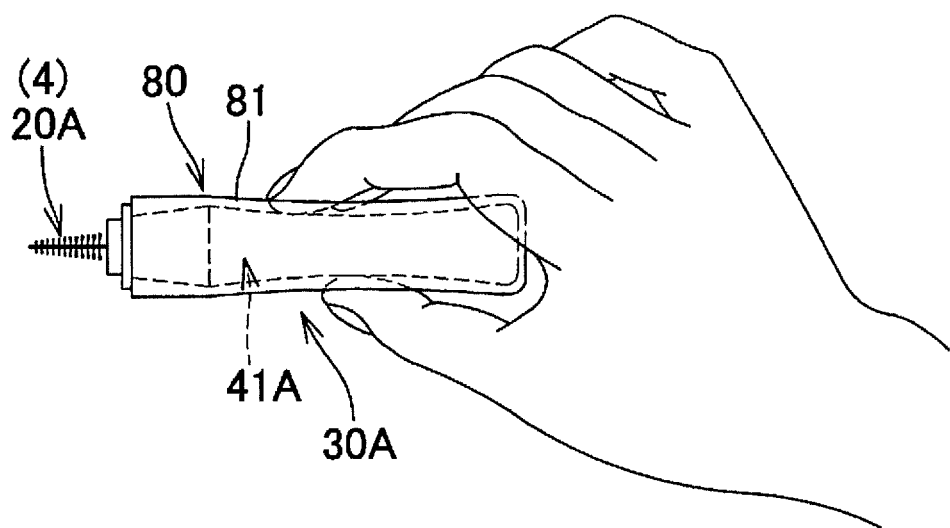
FIG. 9 is an explanatory drawing showing how a user holds a holder mounted to a drug-containing personal hygiene implement and presses a bottle body with fingers.

The holder main body section 81 has a shape of bottomed cylinder, and on a peripheral wall section of the holder main body section 81 are provided two openings 83 through which the bottle body 41A to be stored in the holder main body section 81 can be pressed with fingers from the side. In addition, the two openings 83 are provided in mutually opposed positions. Then, as shown in FIG. 9, at the point of use, a user can put his/her fingers into each of the openings 83 to press side faces of the inside bottle body 41A, thereby being able to discharge a drug. Only one opening 83 or three or more openings 83 may be provided.

As shown in FIG. 8, the holder cap section 82 is detachably put on a distal end of the holder main body section 81. The holder cap section 82 has a streak of annular convex section 84 formed on an inner peripheral surface on the side of a base end section thereof, making it possible to fit the convex section into an annular concave groove 85 at the distal-end section of the holder main body section 81. Note that in order to dry the interdental brush body 20A, which is the personal hygiene body 4, ventholes may be provided on the holder cap section 82.

Figure 10:
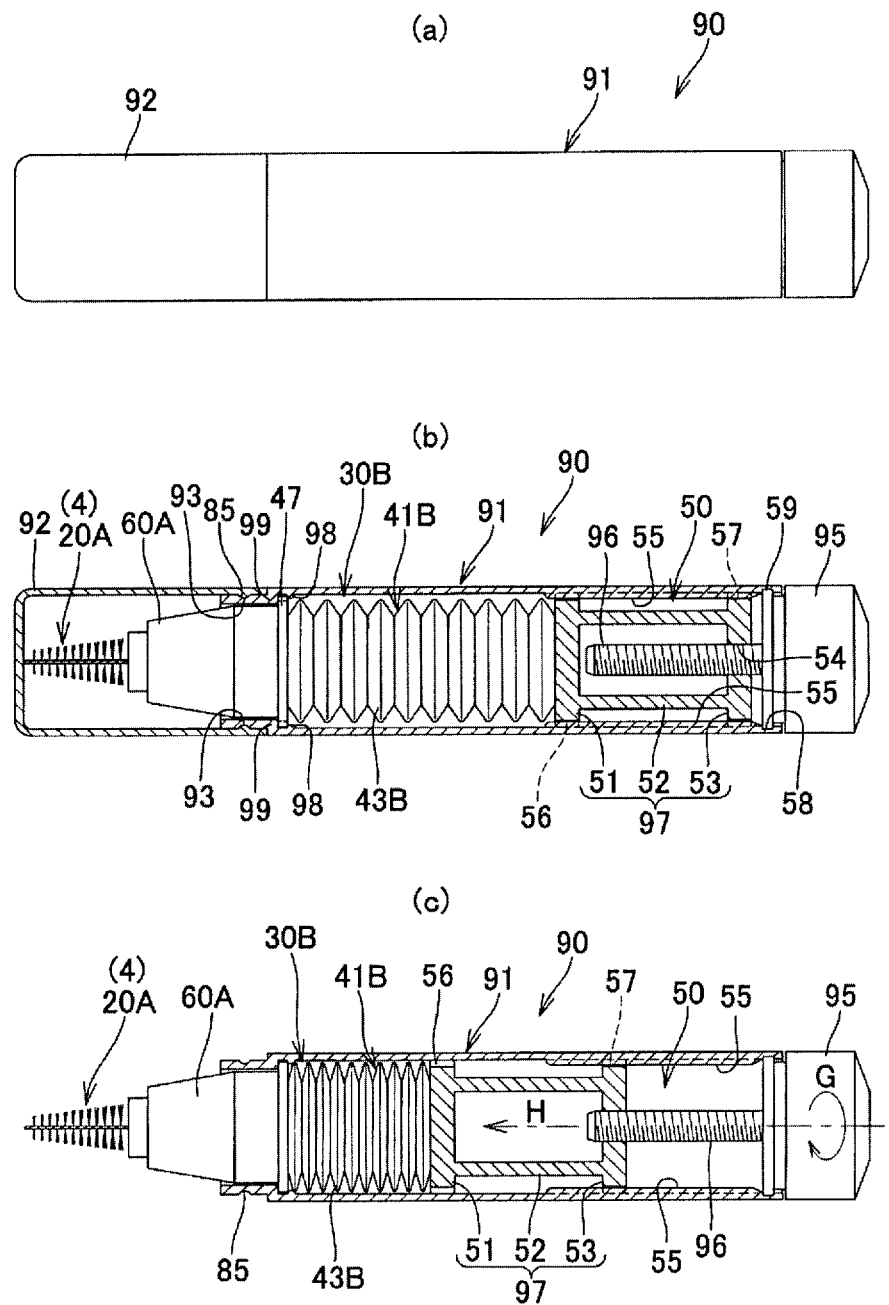
FIG. 10(a) is a side elevation showing a variant of the same holder.
FIG. 10(b) is a vertical cross-sectional view of the same.
FIG. 10(c) is an explanatory cross-sectional view showing how it is used.

FIG. 10 is an explanatory drawing showing other holder example. A holder 90 in this example has a holder main body section 91 capable of storing a bottle body 41B and a holder cap body 92 covering an interdental brush body 20A. Similar to the holder 80, the holder 90 is made from a hard material. A streak of annular convex section 93 is formed on an inner peripheral surface on the side of a base end section of the holder cap section 92. This annular convex section 93 engages in the annular concave groove 85 at the distal end of the holder main body section 91, so that the holder cap section 92 is detachably put on the distal end section of the holder main body section 91.

A drug-containing personal hygiene implement 30B to be attached to the holder 90 is configured such that the bottle body 41B comprises a neck section 60A on the distal-end side and a main body section 43B on the base end side, with a collar-like engaged section 47 provided in the distal-end middle part as a border. Since the main body section 43B is made from soft resin and formed into a bellows shape, it is configured such that it can be freely compressed or deformed in an axial direction. Thus, even if a drug having relatively high viscosity is filled, it can be easily squeezed. The holder main body section 91 is provided with a pressing mechanism 50 which is to be stored from the base end side, and which presses and compresses the bellows-like main body section 43B with a pressing member 97 from the base end side, with the collar-like engaged section 47 latched between engaged sections 98, 99 formed on an inner peripheral surface of the holder main body section 91.

The pressing mechanism 50 includes a screw rod 96 positioned at the shaft center, an operating section 95 rotatably mounted to a base end section of the holder main body section 91 and rotating the screw rod 96, and a pressing member 97 guided to the inner peripheral surface of the holder main body section 91 and mounted movably to an axial direction, and threadably mounted on the screw rod 96 and moving to the axial direction together with rotation of the screw rod 96.

More specifically, the pressing member 97 includes an abutting section 51 which abuts on a base end surface of the main body section 43B of the bottle body 41B, bottom section 53 where a screw hole 54 threaded to the screw rod 96 is provided, and a connecting section 52 for connecting the abutting section 51 and bottom 53. In addition, on the inner peripheral surface of the holder main body section 91, the guide section 55 along the axial direction is a convex streak which engages with the engaged concave sections 56, 57, each formed on outer peripheral surfaces of the abutting section 51 and bottom section 53 of the pressing member 97 and guides the pressing member 97 in an unrotatable manner and movably to the axial direction. Note that the structure which guides the pressing member 97 in an unrotatable manner and movably to the axial direction is not limited to this. A sliding speed of the pressing member 97 can be changed to a desired speed by changing a screw lead angle of the screw rod 96.

In addition, an engaged section 59 of the operating section 95 is detachably engaged with an engaged section 58 of the holder main body section 91. The drug-containing personal hygiene implement 30B can be attached from the base end side by removing the operating section 95 from the holder main body section 91. When the operating section 95 is turned to the arrow G direction, the pressing member 97 threaded to the screw rod 96 which rotates in conjunction with the operating section 95 moves to the arrow H direction. Then, since the engaged section 47 of the bottle body 41B is engaged with the engaged sections 98, 99 provided in the holder main body section 91 and is fixed, the abutting section 51 which abuts on the bottom surface of the bottle body 41B presses and compresses the bottom surface of the bottle body 41B, and the drug filled in the bottle body 41B is squeezed.

In the holder 90, due to restoring force of the compressed holder main body section 91, force facing the base end side (direction opposite to arrow H) acts on the pressing member 97. In order to control it, a ratchet mechanism for preventing inverse rotation of the screw rod 96 may be provided. In addition, it may be acceptable that by further providing a mechanism for opening the ratchet mechanism, the pressing member 97 can be returned to its original position, i.e., a position to set a new bottle body 41B.

With the holder 90 in this variant, provision of the holder composed of a hard material and having the holder main body section capable of storing the bottle body can improve ease of hold and ease of use during use. In addition, rotating the operating section 95 as necessary can adjust an amount of the drug to be discharged. In addition, residue inside the bottle body 41B can be reduced and discharged drug can be prevented from returning to the bottle body 41B. In addition, in the holder 80, since an opening 83 through which the bottle body 41A can be pressed is provided, it is likely that the holder may have constraints in terms of designing of a holder casing and economy. However, with the holder 90 in this variant, there are fewer constraints.

Figure 11:
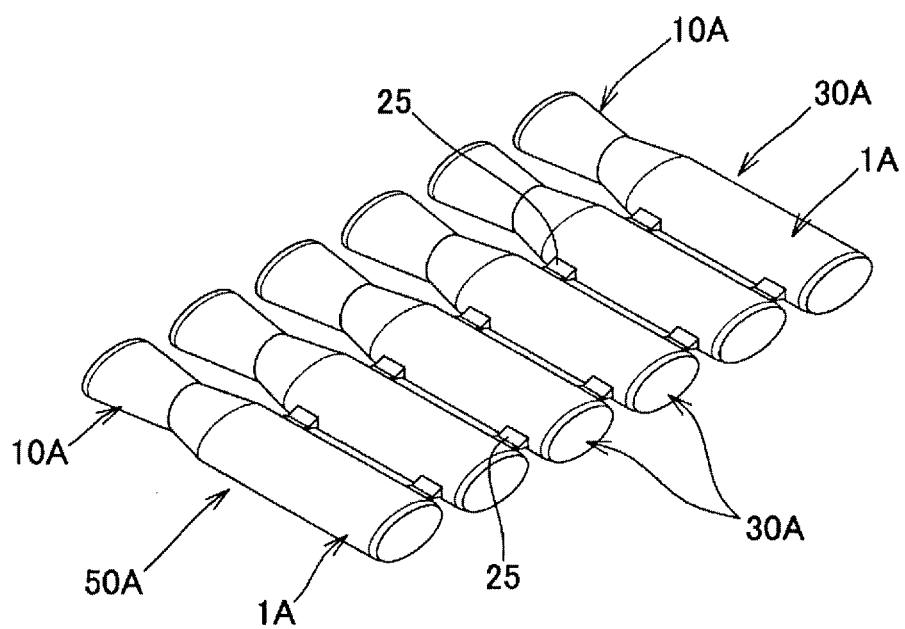
FIG. 11 is an explanatory perspective view showing a configuration example as "multiple container type" wherein the same drug-containing personal hygiene implements are junctually formed.

Although the first embodiment has been described so far, the present invention shall not be limited to those described above. For example, leakage or backflow of a drug may be prevented by providing a check valve in a passage of a cap body. In addition, in the first embodiment, although the drug-containing personal hygiene implement 30 is of a "separate type", which is composed of a single implement, it may be of "multiple container type" in which multiple containers are junctually formed by linearly connecting the drug-containing personal hygiene implements 30A at a part of containers (for example, a die parting line), as shown in FIG. 11. In the example of FIG. 11, bottle bodies 1A of the drug-containing personal hygiene implements 30A are linearly connected at the die parting line 25.

Figure 12:
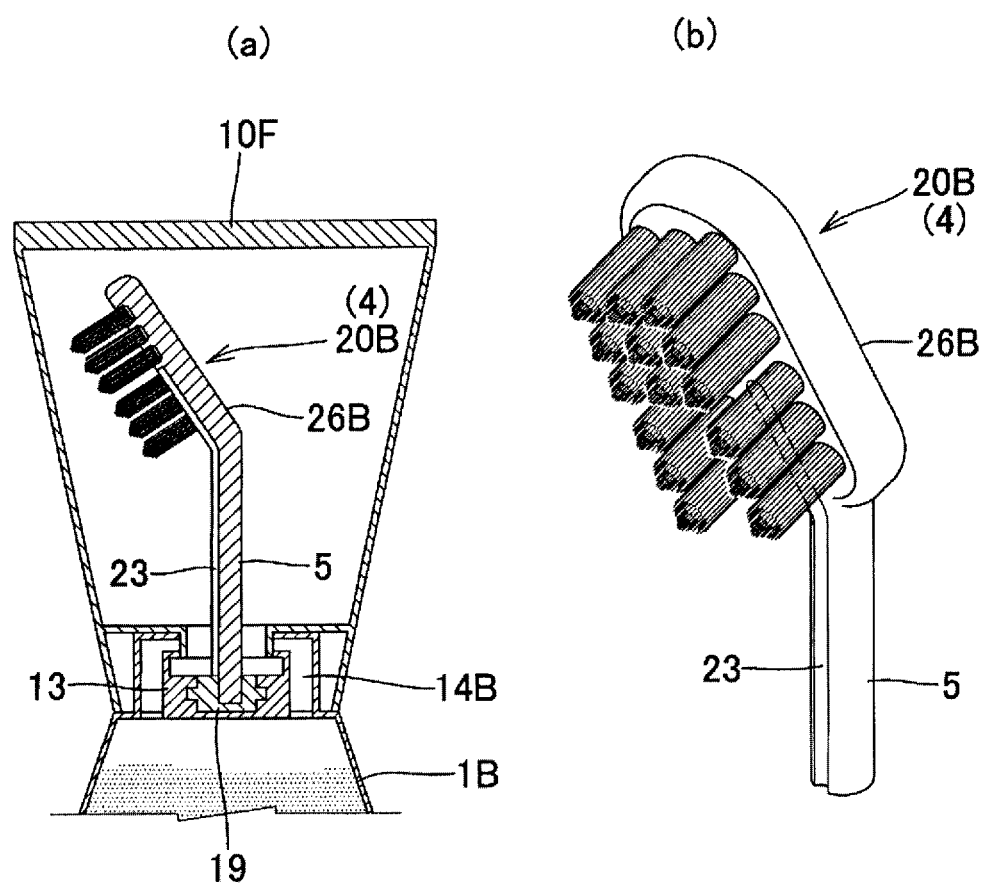
FIG. 12(a) is a vertical cross-sectional view showing a main part of a variant before opening in which a personal hygiene body of the same drug-containing personal hygiene implement is a toothbrush body.
FIG. 12(b) is a perspective view of the same toothbrush body.
Figure 13:
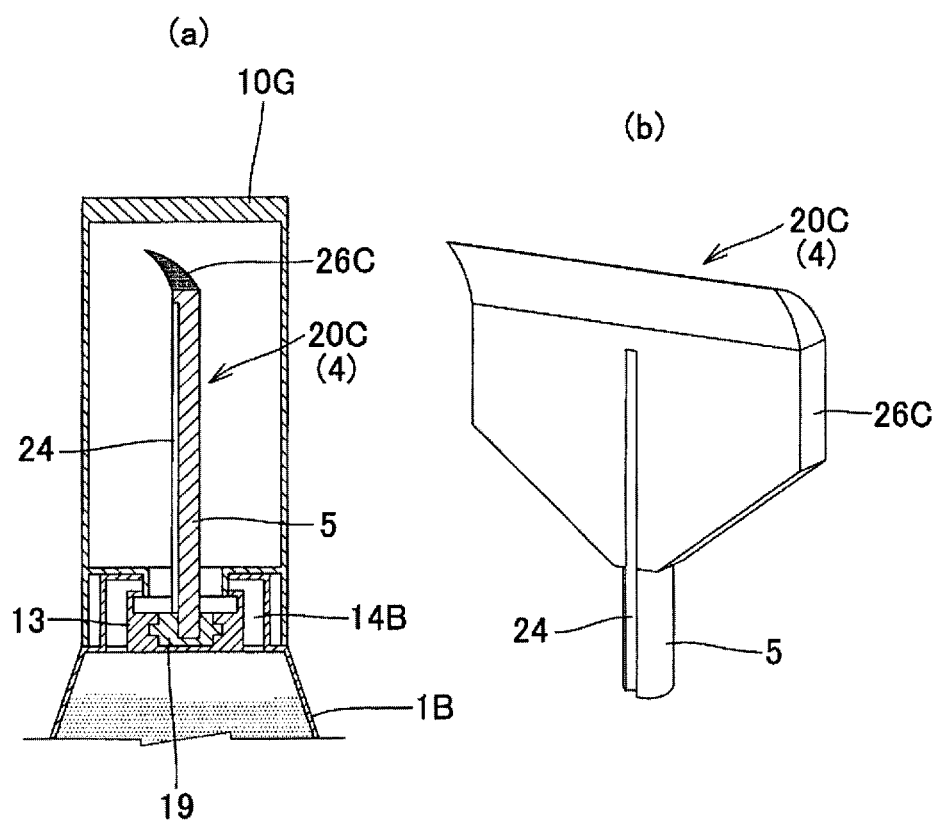
FIG. 13(a) is a vertical cross-sectional view showing a main part of a variant before opening in which a personal hygiene body of the same drug-containing personal hygiene implement is a tongue cleaner body.
FIG. 13(b) is a perspective view of the same tongue cleaner body.

In addition, although the case in which the personal hygiene body 4 is the interdental brush body 20A in which the personal hygiene section 6 is the interdental brush section 26A was described, the invention is not limited to this. For example, the case in which the personal hygiene body is the toothbrush body 20B in which the personal hygiene section 6 is the toothbrush section 26B, as shown in FIG. 12, or the case in which the personal hygiene body is the tongue cleaner body 20C in which the personal hygiene section 6 is the tongue cleaner section 26C, as shown in FIG. 13, are also preferred embodiments. In the examples shown in FIG. 12 and FIG. 13, the configuration is such that concave grooves 23, 24 along the axial line direction are provided in the shaft section 5 of the toothbrush body 20B or tongue cleaner body 20C, and the drug 2 reaches the personal hygiene section 6 along the concave grooves 23, 24.

Based on FIG. 14 to FIG. 25, a second embodiment of the present invention will be described in the following.

Figure 14:
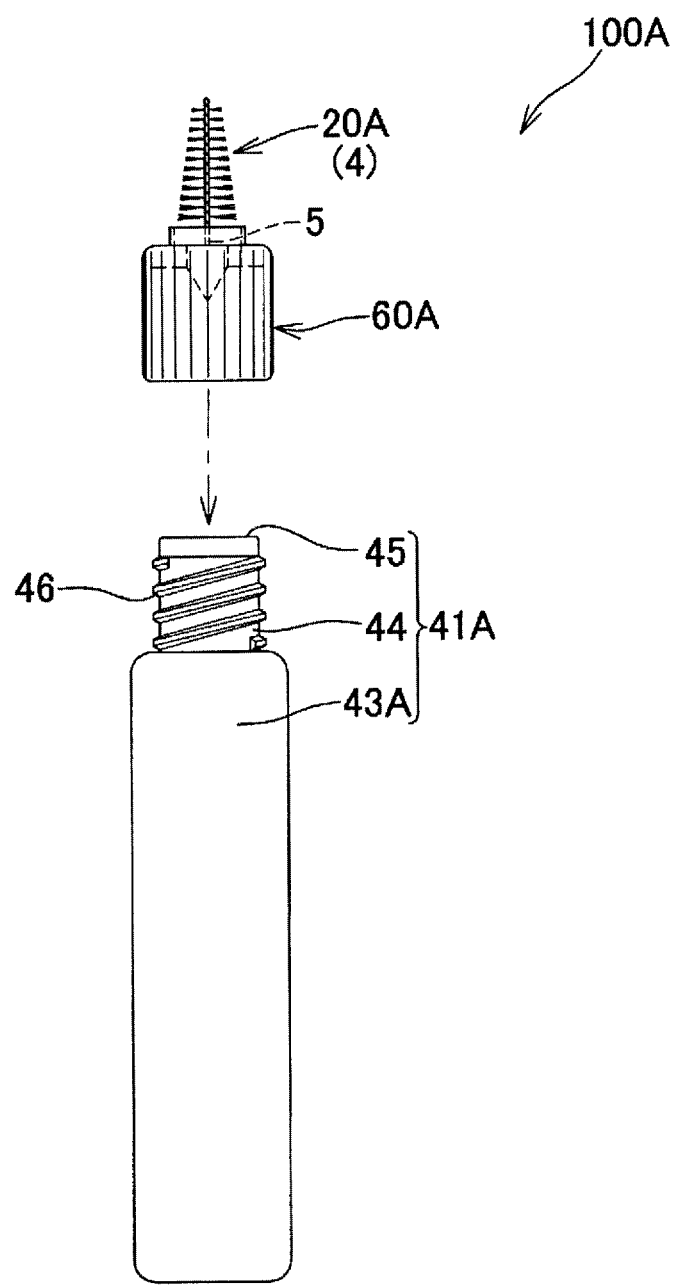
FIG. 14 is an explanatory drawing of a drug-containing personal hygiene implement according to a second embodiment of the present invention.
Figure 15:
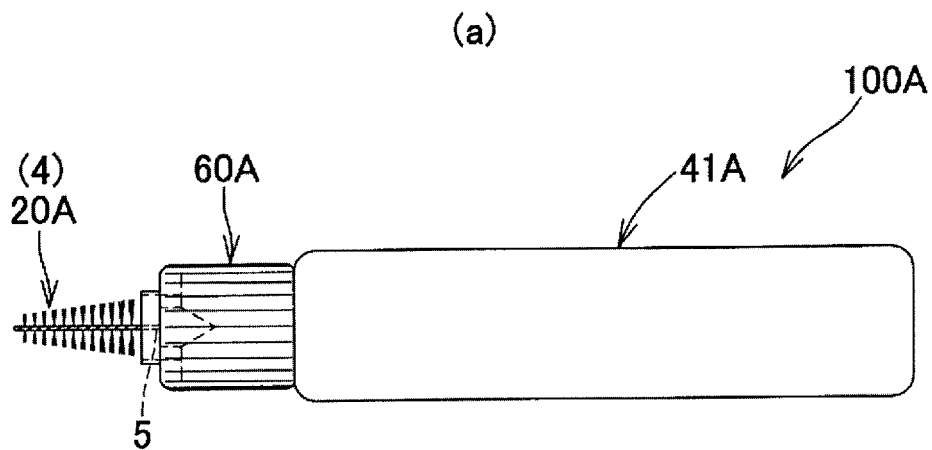
FIG. 15(a) is a side elevation showing an overall configuration of the same drug-containing personal hygiene implement.
FIG. 15(b) is a vertical cross-sectional view of the same.
Figure 15:
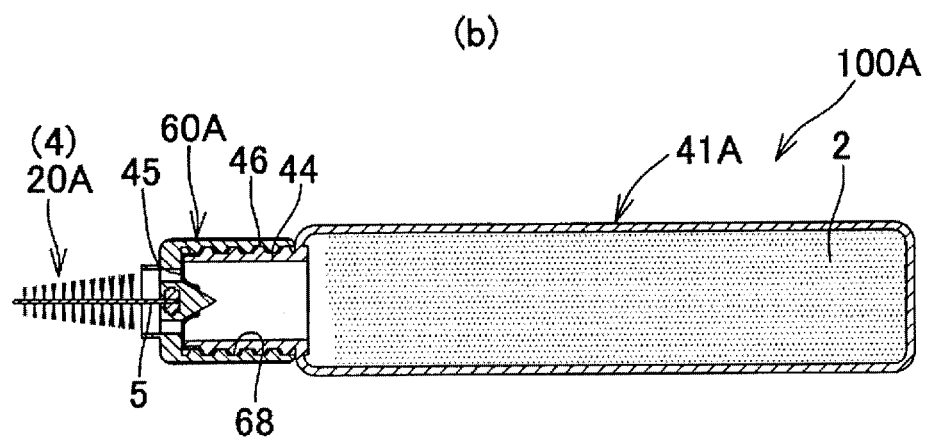

As shown in FIG. 14, a drug-containing personal hygiene implement 100A of the embodiment includes a bottle body 41A in which a seal section 45 is provided at a distal end of a neck section 44 and a drug 2 is stored in the interior thereof in a hermetically-sealed state, a cap member 60A attached to the neck section 44 of the bottle body 41A, and an interdental brush body 20A, which is a personal hygiene body 4 protruding on an outer surface 62 of an upper wall section 66 on a distal end side of the cap member 60A. As shown in FIG. 14, the bottle body 41A consists of a main body section 43A, the tubularly projecting neck section 44, and the seal section 45 located at the distal end of the neck section 44, and a screw section 46 is provided on an outer circumference of the neck section 44. Then, by opening operation of attaching the cap member 60A to the bottle body neck section 44, a protrusion 63A, to be described below, penetrates the seal section 45, thus making it possible to supply the drug stored in the bottle body to a periphery of a base end section of the interdental brush body 20A through a passage 64A.

Similar to the first embodiment, such a bottle body 41A is molded into a state in which the drug 2 is hermetically contained inside, by the aseptic filling and packaging manufacturing machine in a series of blow-fill-seal (BFS) processes. The bottle body 41A is configured such that after being filled with the drug 2, it is sealed by thermally adhering, as the seal section 45, a film of the same material as the main body section 43A to an opening at the distal end of the neck section 44. The seal section 45 can also be formed by adhering a member such as a sheet or film and the like made from aluminum, rubber, synthetic resin, silicon and the like, in the course of insert molding in the BFS process. A material similar to that of the bottle body 1A in the first embodiment described above may be adopted for the material of the bottle body 41A. In addition, the drug 2 to be stored in the bottle body 41A may also be selected as appropriate, depending on a type of a distal-end personal hygiene body 4, as with the first embodiment described above.

Figure 16:
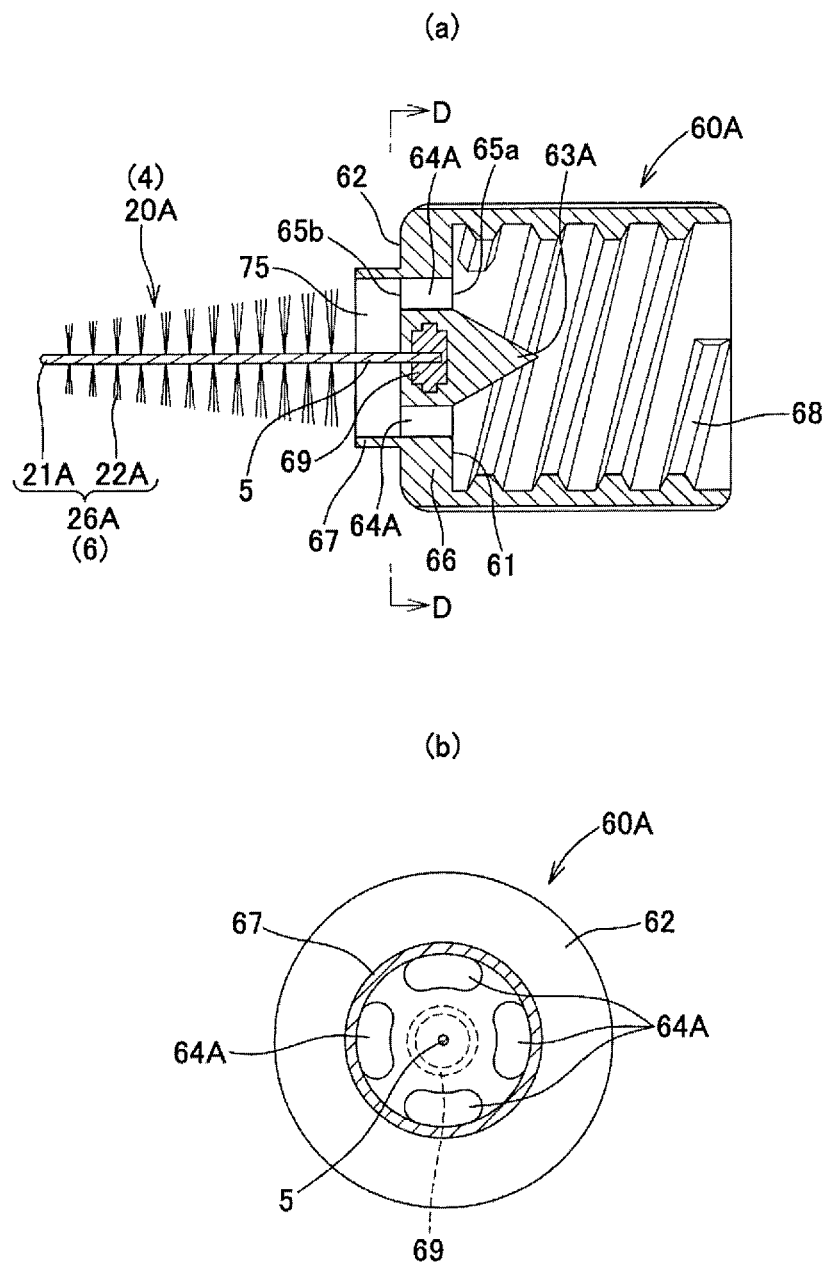
FIG. 16(a) is a vertical cross-sectional view showing a cap body and personal hygiene body of the same.
FIG. 16(b) is a transverse cross-sectional view of D-D of FIG. 16(a).
Figure 17:
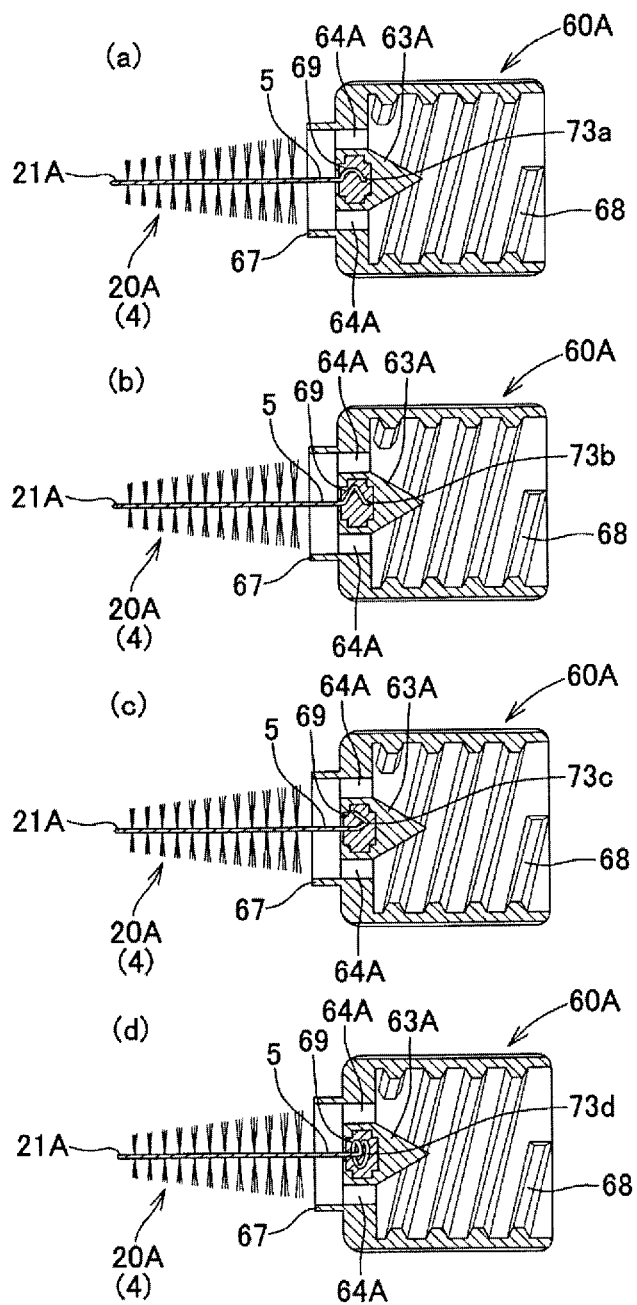
FIG. 17(a) to FIG. 17(d) are cross-sectional views showing variants of a shaft section of the same drug-containing personal hygiene implement.

In an inner periphery of the cap member 60A, as shown in FIG. 15(b) and FIG. 16, female screw sections 68 to which screw sections 46 on the outer circumference of the neck section 44 are threadably mounted are formed, and the cap member 60A having the interdental brush body 20A, which is the personal hygiene body 4, and bottle body 41A are configured to be mutually detachable. Thus, when the drug in the bottle body 41A is used up, the cap member 60A is removed and attached to a new bottle body 41A, thereby reusing the cap member 60A. In the cap member 60A, not only a protrusion 63A shaped like a tapered cone is provided on the side of an inner surface 61 facing the seal section 45 of the bottle body 41A, but also a passage 64A for drug distribution leading from the side of an inner surface 61 to the side of an outer surface 62 is provided. In a drug-containing personal hygiene implement 100A when it is used as a portable implement, a diameter on the outer surface 62 side of the upper wall section 66 of the cap member 60A is set to size of brush diameter of a brush section 72 plus 1 mm, by way of example.

The interdental brush body 20A includes an interdental brush section 26 and shaft section 5, as with the first embodiment described above, and an embedded section 69 which is similarly buried in the cap member 60A is provided in the base end section of the shaft section 5. Similar to the first embodiment described above, shape of the base end section of the shaft section 5 to be buried in the embedded section 69 may also be deformed. FIG. 17(a) is an example in which the base end section 73a is bent in a semicircular manner. FIG. 17(b) is an example in which the base end section 73b is bent in a dogleg manner. FIG. 17(c) is an example in which the base end section 73c is bent like letter J (into a hook). FIG. 17(d) is an example in which the base end section 73d is bent in a spiral manner.

Figure 18:
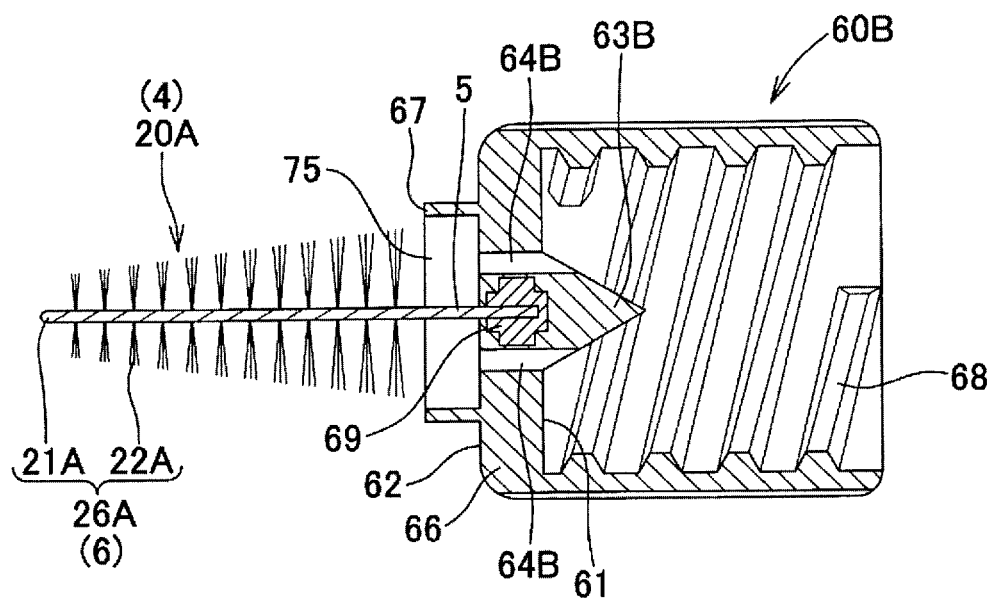
FIG. 18 is a vertical cross-sectional view showing a variant of a cap body of the same drug-containing personal hygiene implement.
Figure 19:
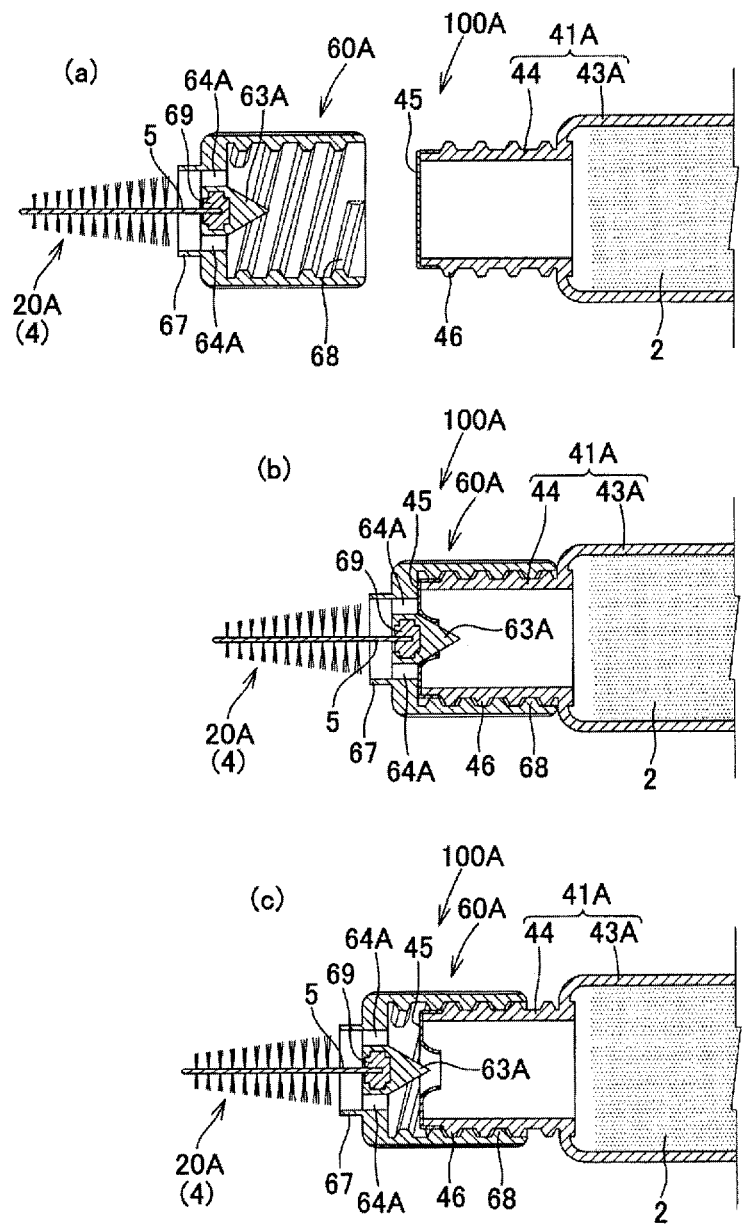
FIG. 19(a) to FIG. 19(c) are explanatory drawings showing how the same cap body is mounted to a neck section and opened.

On the inner surface of the upper wall section 66 of the cap member 60, the pointed cone-shaped protrusion 63A protrudes toward the inner side (base end direction) of the cap member. On the upper wall section 66, the passage 64A for guiding the drug 2 to brush sections 22A of the interdental brush body 20A is also formed. The passage 64A is a through-bore communicating from the inner surface 61 side of the upper wall section 66 to the outer surface 62 side. An opening 65a on the inner surface 61 side is formed around the root of the protrusion 63A, while an opening 65b located on the outer surface 62 side constitutes a discharge opening facing the interdental brush body 20A. Note that the position of the passage 64A is not limited to this, and the passage 64A may be provided at a desired position on the upper wall section 66 of the cap member 60A. As shown in FIG. 18, for example, the passage 64A may be a through-bore communicating from the outer peripheral surface on the side of the root of the protrusion 63B of the cap member 60B to the outer surface 62 side of the upper wall section 66.

On the outer surface 62 side of the cap member 60A is provided a tubular protrusion 67 which projects tubularly, and the interdental brush body 20A protrudes on the inner side of the tubular protrusion 67, and the passage 64A opens. A concave space inside the tubular protrusion 67 functions as a trap section 75 for the drug 2 discharged from the opening of the passage 64A, and can not only prevent dripping of the drug 2 applied to the interdental brush body 20A but also control splattering even when the drug 2 is squeezed in large amounts.

In the drug-containing personal hygiene implement 100A in such an embodiment, as shown in FIG. 19(a) to FIG. 19(b), as a result of attaching the cap member 60A to the neck section 44 of the bottle body 41A by threading, the protrusion 63A breaks and penetrates the seal section 45, thereby opening a part of the seal section 45 of the bottle body 41A. Then, the drug 2 can be supplied to the periphery of the base end section of the interdental brush body 20A through the passage 64A, by slightly loosening the cap member 60A. Then, as shown in FIG. 19(c), an amount of the drug 2 to be discharged increases as the cap member 64A is loosened, thus making it possible to adjust the amount of discharge. If the implement is not used, it is sealed by firmly closing the cap member 60A, thereby making it possible to prevent leakage of the drug 2.

Figure 20:
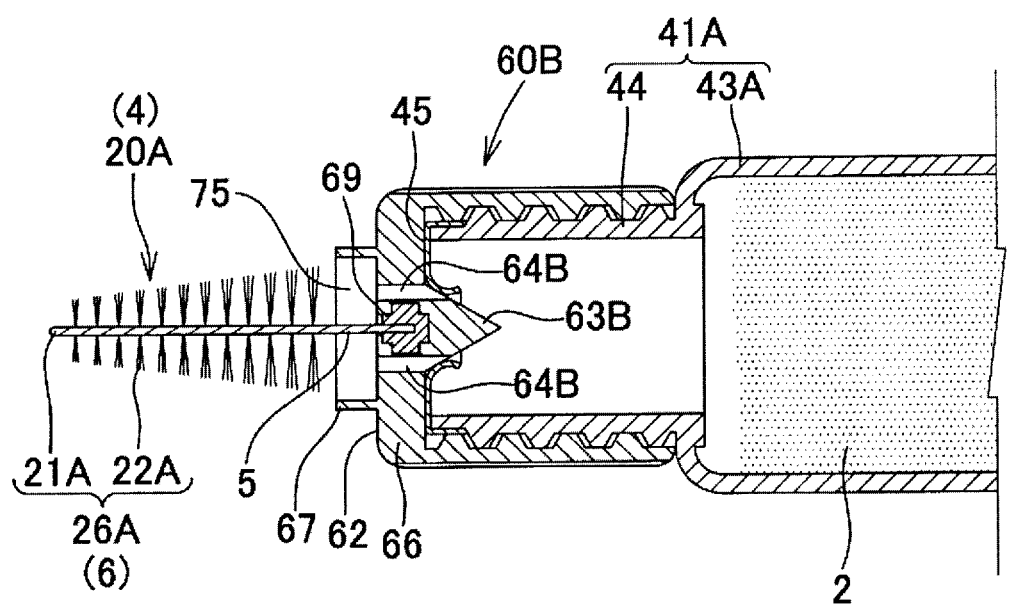
FIG. 20 is a vertical cross-sectional view of a main part showing a state in which a cap body according to the same variant is mounted to a neck section.

FIG. 20 shows a state in which the cap member 60B according to the variant described in FIG. 18 is attached. The seal section 45 of the cap member 60B opens by the protrusion 63B of the cap member 60B penetrating the seal section 45. In this example, since a through-hole 64B opens to the root side middle part of the outer peripheral surface of the protrusion 63B, the drug can be discharged via the through-hole 64B without loosening the cap member 60B. Also in this example, the supply amount of the drug 2 can be easily adjusted by opening and closing of the cap member 60B.

A method for manufacturing the drug-containing personal hygiene implement 100A of the embodiment will be described in the following.

Similar to the first embodiment, the drug-containing personal hygiene implement 100A is manufactured in a publicly known blow-fill-seal process by a sterile (aseptic) filling and packaging manufacturing machine. The bottle body 41A is manufactured by blow molding. In this process, the neck section 44 and main body section 43A following it are molded. First, molten resin is extruded into the interior of a die in sterile air. Then, the hollow cylindrical main body section 43A is molded, by feeding compressed air from an opening region through which the resin is extruded, and inflating the resin. The opening region is bound in the die and not inflated during blow molding, and the neck section 44 is molded.

Then, the drug 2 is filled by a filling nozzle. Similar to the first embodiment described above, desired viscosity of the drug 2 is selected, from the standpoints of discharging performance from the opening 65b of the passage 64A, prevention of splattering of the drug 2 in the trap section 75, and promotion of capillary phenomenon in the brush shaft section 71. After being filled with the drug 2, the seal section 45 is formed by thermally adhering a film of the same material as the main body section 43A to the distal end of the neck section 44 and sealing it, and the bottle body 41A in which the drug is contained is thereby formed. Note that a nitrogen purge may be performed before sealing if the drug 2 easily oxidizes. Similar to the first embodiment described above, the interdental brush body 20A is also manufactured by an interdental brush manufacturing machine, using filaments of nylon and the like and metallic wires (or metallic wires coated with synthetic resin).

The cap member 60A is manufactured by the injection molding process. The interdental brush body 20A is integrally fixed onto the upper wall section 66, by insert molding the embedded section 69 formed on the base end section of the shaft section 5 when molding the cap member 60A. Specifically, after the embedded section 69 on the base end side of the interdental brush body 20A is inserted into the die for molding the cap member 60A, the die is filled with synthetic resin, which is a material of the cap member 60A, and the synthetic resin is hardened, the die is opened and the cap member 60A is removed. With this, the interdental brush body 20A and cap member 60A are integrated by burying the base end section of the shaft section 5 in the upper wall section 66 of the cap member 60A, and thus the cap member 60A to which the interdental brush body 20A is provided is formed. Then, the cap member 60A is attached to the bottle body 41A, and the drug-containing personal hygiene implement 100A is complete.

Figure 21:
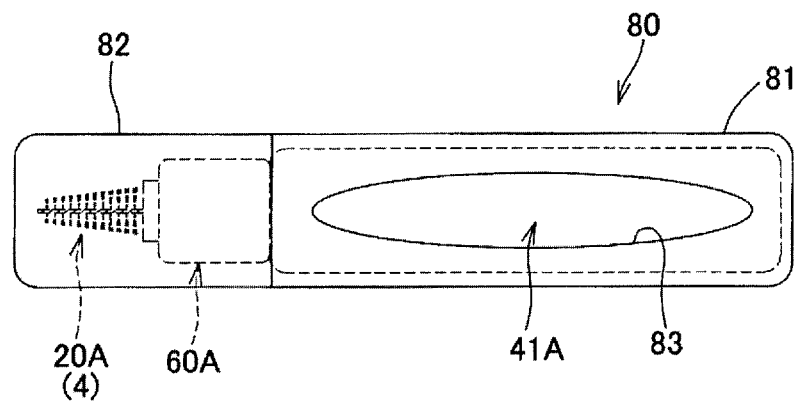
FIG. 21(a) is a side elevation showing a state in which a holder is mounted to the same drug-containing personal hygiene implement.
FIG. 21(b) is a vertical cross-sectional view of the same holder.
Figure 21:
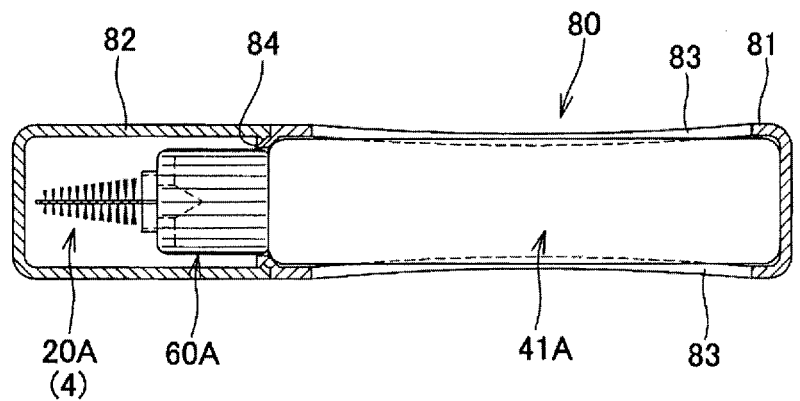
Figure 22:
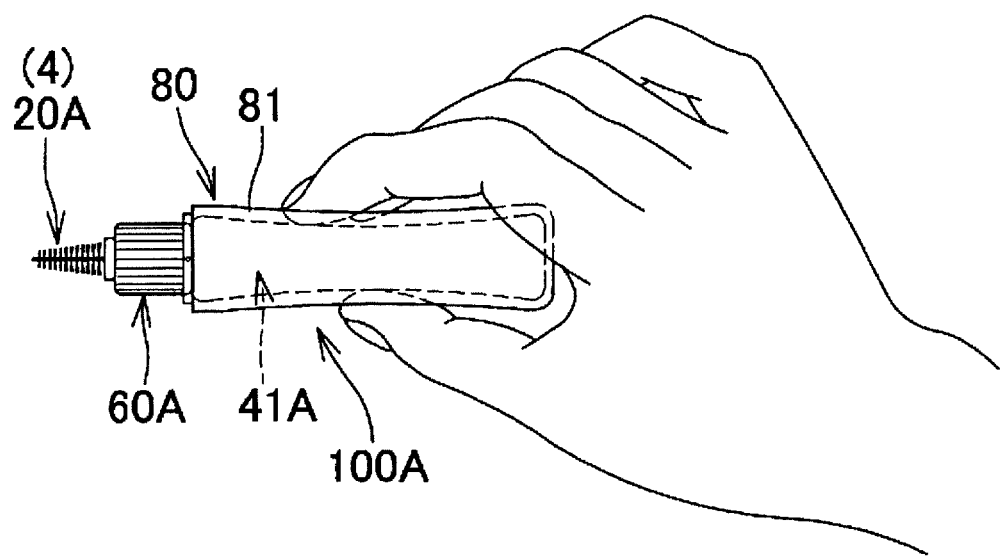
FIG. 22 is an explanatory drawing showing how a user holds a holder mounted to a drug-containing personal hygiene implement and presses a bottle body with fingers.
Figure 23:
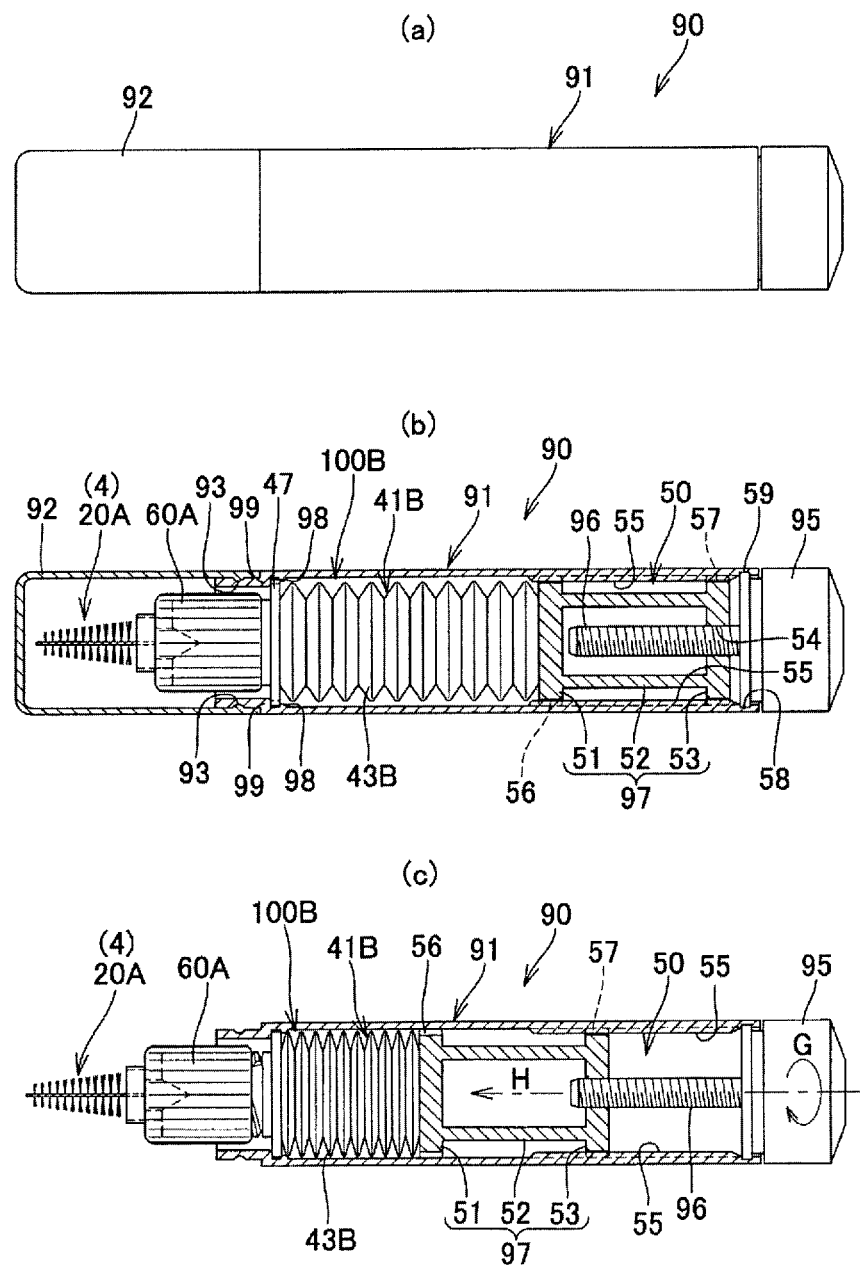
FIG. 23(a) is a side elevation showing a variant of the same holder.
FIG. 23(b) is a vertical cross-sectional view of the same.
FIG. 23(c) is an explanatory cross-sectional view showing how it is used.
Figure 24:
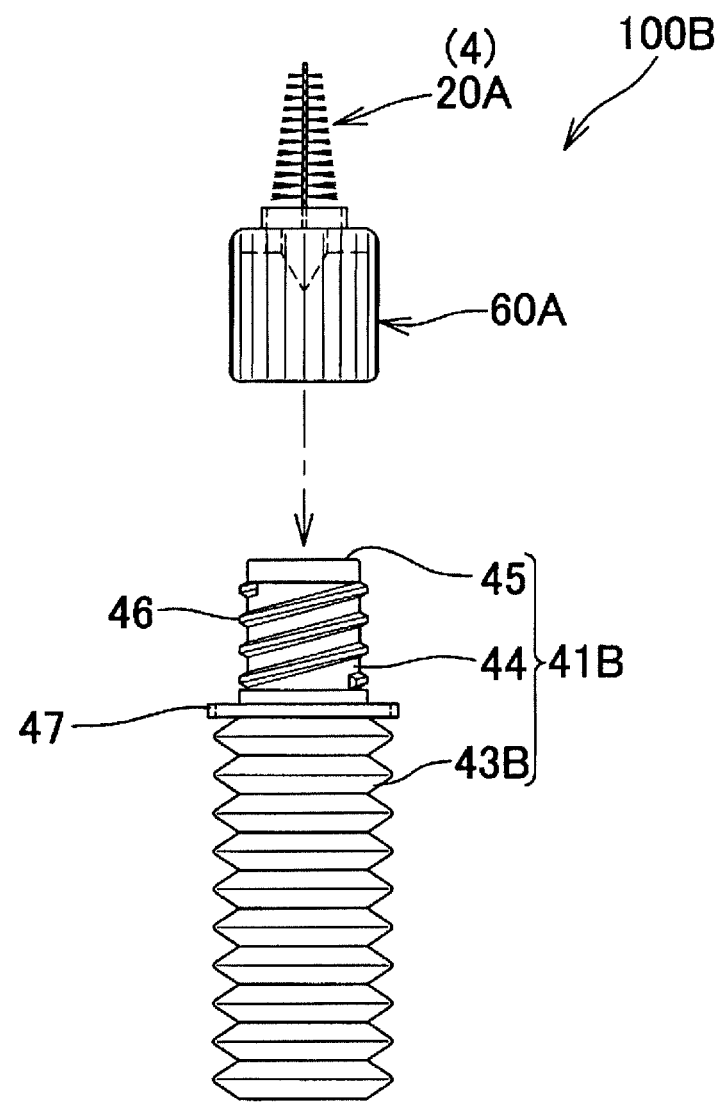
FIG. 24 is an explanatory drawing showing a variant of a bottle body.

Similar to the first embodiment described above, in the drug-containing personal hygiene implement 100A of the embodiment, it is preferable to provide a holder 80(90) as shown in FIG. 21 to FIG. 23. The holder 80 (90) includes a holder main body section 81 (91) capable of storing a bottle body 41A and holder cap section 82(92) covering a cap member 60A and an interdental brush body 20A, which is a personal hygiene body 4. The drug-containing personal hygiene implement 100B attached to the holder 90 has a collar-like engaged section 47 provided on a base end side of a neck section 44, and configured such that the main body section 43B of the bottle body 41B can be axially compressed or deformed, by being composed of soft resin and formed in bellows shape. The main body section 43B can be contracted in an axial line direction by pressing a terminal part. Making the main body section 43B in a bellows shape enables the drug to be easily squeezed even if the drug has relatively high viscosity. In addition, the holder 80 (90) is basically identical to those described in FIG. 8 to FIG. 10 in the first embodiment above. The same symbols are assigned to the same structures, a description of which is omitted.

Figure 25:
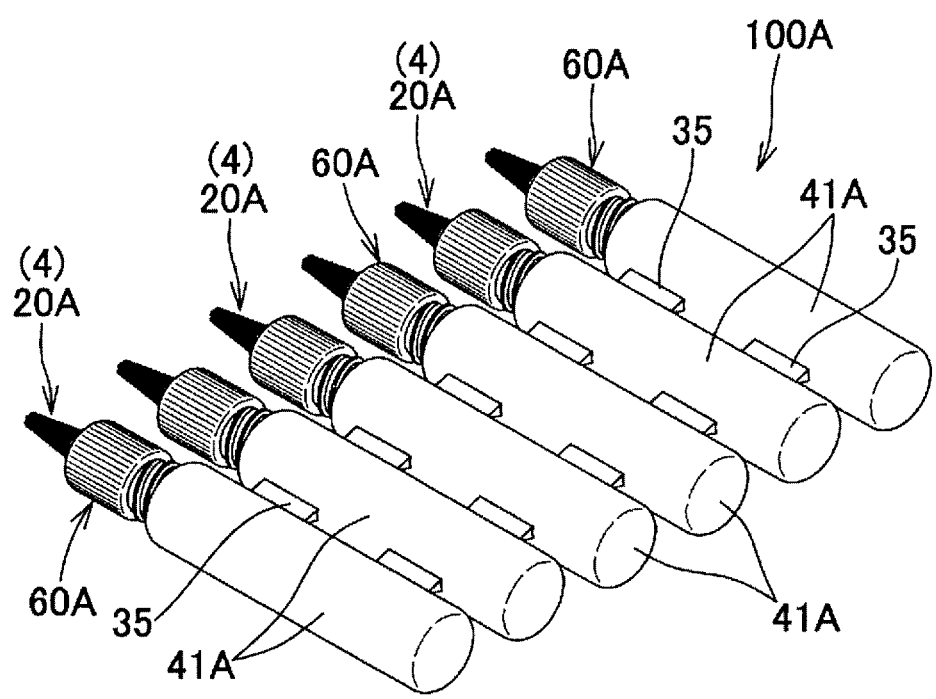
FIG. 25 is an explanatory perspective view showing a configuration example as "multiple container type" wherein the same drug-containing personal hygiene implements are junctually formed.

Although the second embodiment has been described so far, similar to the first embodiment, for example, leakage or backflow of a drug may be prevented by providing a check valve in the passage 64A. In addition, as shown in FIG. 25, the implement may be of "multiple container type" in which multiple containers are junctually formed by linearly connecting the drug-containing personal hygiene implements 100A at a part of containers (for example, a die parting line). In the example of FIG. 25, the bottle bodies 41A of the drug-containing personal hygiene implements 100A are linearly connected at the die parting line 35. In addition, similar to the first embodiment, the personal hygiene body 4 is not limited to the interdental brush body 20A. As shown in FIG. 12 and FIG. 13 for example, the case in which the personal hygiene body 4 is the interdental brush body 20B or tongue cleaner body 20C is also a preferred embodiment.

Based on FIG. 26 to FIG. 36, a third embodiment of the present invention will be described in the following.

Figure 26:
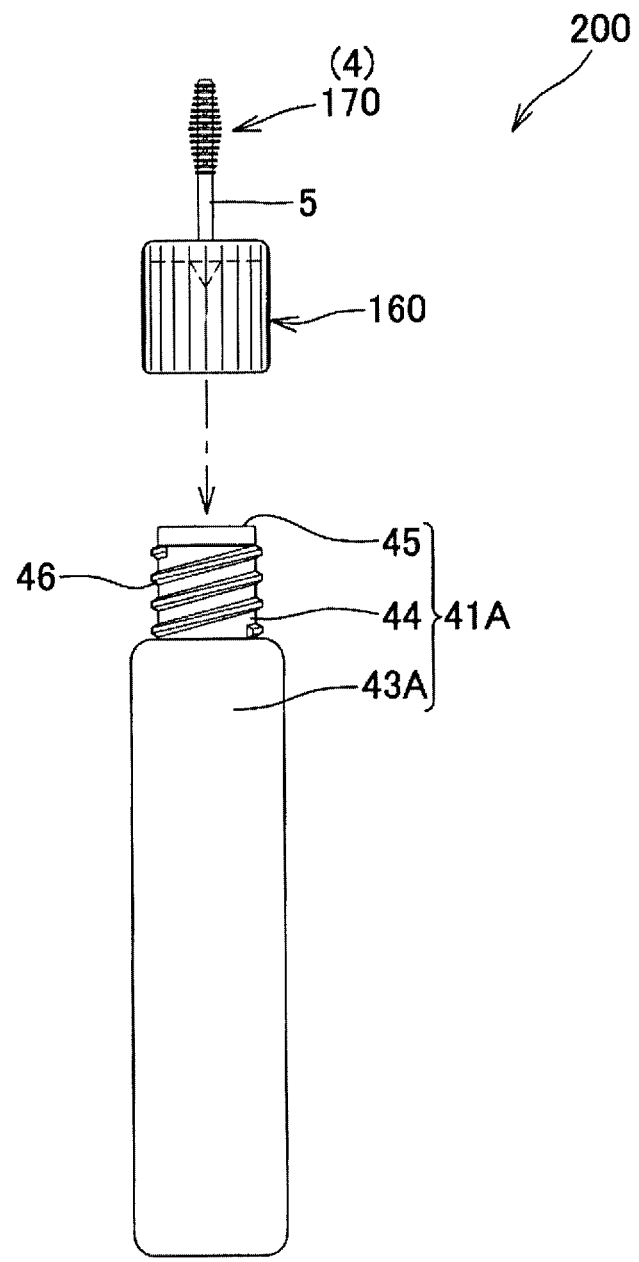
FIG. 26 is an explanatory drawing of a drug-containing personal hygiene implement according to a third embodiment of the present invention.
Figure 27:
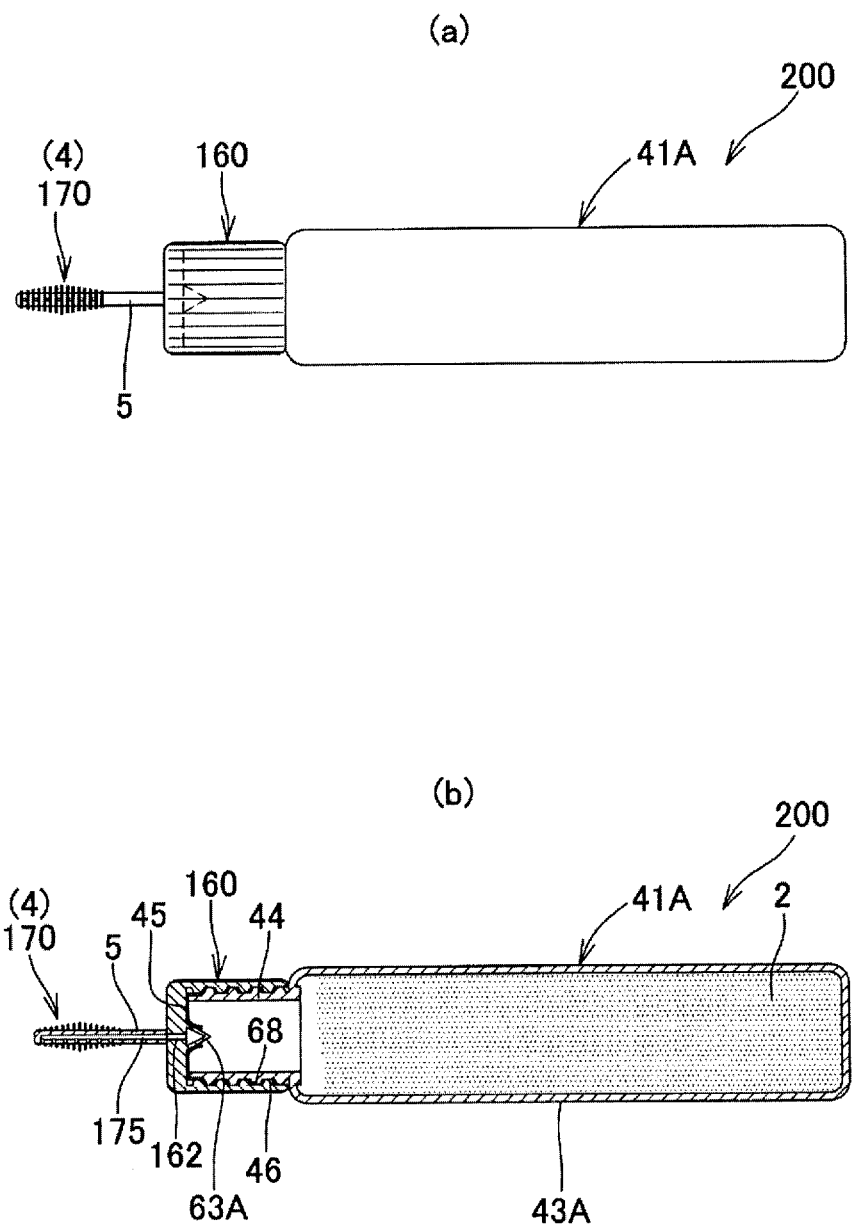
FIG. 27(a) is a side elevation showing an overall configuration of the same drug-containing personal hygiene implement.
FIG. 27(b) is a vertical cross-sectional view of the same.

As shown in FIG. 26 and FIG. 27, a drug-containing personal hygiene implement 200 of the embodiment is designed such that by opening operation of attaching a cap member 160 to a neck section 44 of a bottle body 143, a protrusion 63A on an inner surface side of the cap member 160 penetrates a seal section 45 of the bottle body 143, thus making it possible to supply a drug 2 to a flow passageway 175 provided in an interior of a shaft section of an interdental brush body 170, which is a personal hygiene body 4, via a through-hole 162. Similar to the second embodiment described above, the drug-containing personal hygiene implement 200 of the embodiment includes the bottle body 41A in which the drug 2 is stored in a hermetically sealed state, the cap member 160 attached to an opening at a distal end of the bottle body 41A, and the interdental brush body 170, which is the personal hygiene body protruding on an upper surface side of the cap member 160 in an axial line direction of the bottle body 41A. Basically, the bottle body 41A and drug 2 are similar to the second embodiment described above, and the same symbols are assigned to the same structures, a description of which is omitted.

In addition, a method for manufacturing a drug-containing personal hygiene implement 200 is also similar to the second embodiment described above. The drug-containing personal hygiene implement 200 is manufactured by a sterile filling and packaging manufacturing machine in a series of blow-fill-seal (BFS) processes. The blow-fill-seal process is characterized in that a sterile drug can be manufactured in a sterile container in a sterile environment. Thus, this enables long-term storage of drugs without blending preservatives such as paraben or alcohol and the like, also making it possible to manufacture a drug-containing personal hygiene implements of disposable type with no preservative blended.

On the inner peripheral surface of the cap member 160, female screw sections 68 threadably mounted to screw sections 46 provided in the neck section 44 of the bottle body 41A are provided, and configured to be detachable to the bottle body 41A. Thus, the configuration is such that when the drug 2 is used up, the cap member 160 is removed and can be attached to a new bottle body 41A. In addition, the protrusion 63A is provided on an inner surface side facing the seal section 45. On the inner surface side of the upper wall section 66 of the cap member 160, the pointed cone-shaped protrusion 63A protrudes toward the base end side. In addition, on the protrusion 63A and upper wall section 66 is formed a through-hole 162 which opens on the outer peripheral surface of the protrusion 63A and is in communication with a flow passageway 175 in the shaft section 5 of the interdental brush body 170, which is the personal hygiene body 4.

Figure 28:
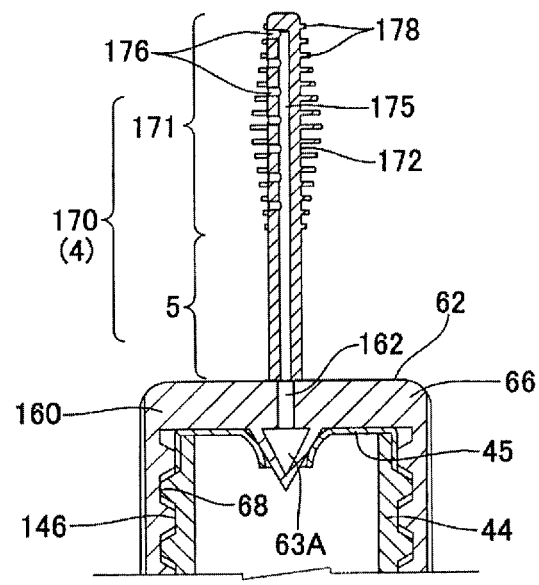
FIG. 28 is a vertical cross-sectional view showing a cap body and personal hygiene body of the same.
Figure 29:
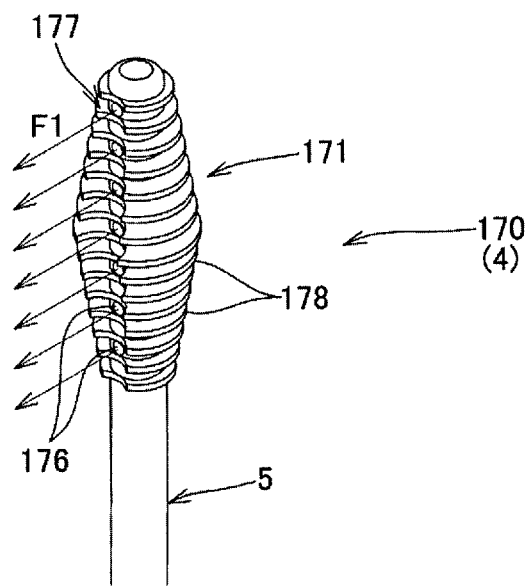
FIG. 29 is a perspective view of the same personal hygiene body.

As shown in FIG. 28 and FIG. 29, the interdental brush body 170, which is the personal hygiene body 4, includes an interdental brush section 171 including a brush shaft section 172 and multiple brush strips 178 having some notches, and a shaft section 5 which continues to a base end side of the brush shaft section 172 and in which a base end section is supported by the cap member 162. In order not to damage gums, for example, the entire interdental brush body 170 or at least brush strips 17 are molded by natural rubber, synthetic rubber, soft synthetic resin, or thermoplastic elastomer. An outline of the interdental brush body 170 may be shaped like a drum whose center part is swollen, as shown in FIG. 28 or spirally shaped. In the brush shaft section 172 and the shaft section 5 which follows it, a flow passageway 175 is provided which is in axially communicated with the interior. In the brush shaft section 172 are provided multiple discharge paths 176 which are in communication with the flow passageway 175 and open at a position among the brush strips 178.

Although the inner diameter of the flow passageway 175 and discharge paths 176 can be changed as appropriate, it is preferably from 0.4 mm to 1.0 mm. The discharge paths 176 are alternately provided at positions of those among the brush strips 178 along the axial direction, in a same direction (direction of F1 in the figure) and in parallel, and openings of the discharge paths 176 are linearly aligned with the axial direction. Then, each brush strip 178 has a notch provided in the direction of the opening, and is configured such that the drug discharged among the brush strips 178 moves to a position between adjacent brush strips through the notch, so that the drug can extend to the entire interdental brush section 171. With such notches, the drug can extend without the need to provide an opening of the discharge path at every position among the brush strips 178, thus making it possible to avoid reduction in strength due to the discharge path. However, any structure other than such structure may be adapted.

The shaft section 5 of the interdental brush body 170 is fixed onto the outer surface 62 of the upper wall section 66 of the cap member 160. In addition, it is preferable that the base end section of the shaft section 5 of the interdental brush body 170 is buried and fixed in the upper wall section 66 during molding of the cap member 160. In addition, it is also possible to form the structure of the above-mentioned protrusion 63A on the base end section of the shaft section 5, thereby integrally molding the shaft section 5 and the upper wall section 66 with the shaft section 5 penetrating the upper wall section 66. Preferably, length of the interdental brush body 170 along the axial direction is set to 10 to 22 mm.

With the drug-containing personal hygiene implement 220 of the embodiment, as shown in FIG. 28, by attaching the cap member 160 to the neck section 44 of the bottle body 41A as the cap member 160 is rotated and threaded, the protrusion 63A of the cap member 160 crimps the seal section 45 of the cap member 160 and penetrates the seal section 45. By the protrusion 63A of the cap member 160 penetrating the seal section 45 of the bottle body 41A, a part of the seal section 45 of the bottle body 41A opens. Then, the drug 2 stored in the bottle body 41A is supplied among the brush strips 178 via the through-hole 162, flow passageway 175, and discharge paths 176.

Although the personal hygiene body 4 is the interdental brush body 170 in this example, it may take other form. For example, a toothbrush body in which the personal hygiene section is a toothbrush section, a tongue cleaner body in which the personal hygiene section is a tongue cleaner section, a toothpick body in which the personal hygiene section is a tapered drug discharge section, a tooth surface cleaning body in which the personal hygiene body is a tooth surface cleaning section, or a drug application body in which the personal hygiene body is a drug application section is preferred. Then, also in these forms, similar to the interdental brush body 170 described above, the drug is supplied to the personal hygiene section through the flow passageway in the interior of the shaft section 5 and discharged from the discharge opening.

Figure 30:
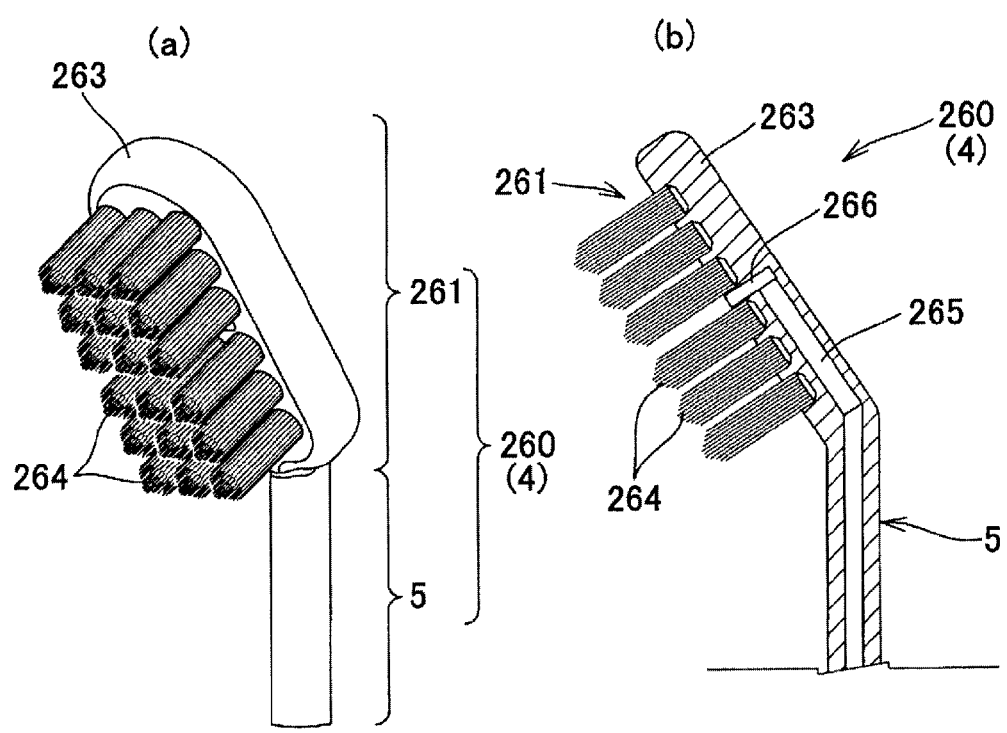
FIG. 30 are a perspective view showing a toothbrush body and a vertical cross-sectional view of the same.

FIG. 30 shows an example in which a personal hygiene body 4 is a toothbrush body 260 in which a personal hygiene section is a toothbrush section 261. The toothbrush section 261 includes a head 263 and brush hair 264 made from synthetic resin. In a shaft section 5 and head 263, a flow passageway 165 through which a drug flows is provided, and the structure is such that the brush hair 164 discharges the drug from a discharge path 266 which opens to the head surface on the projection side, and thus the drug is supplied to the brush air 164. Preferably, the inner diameter of the flow passageway 265 and discharge path 266 is 0.4 mm to 1.0 mm. In addition, preferably, length of the brush hair is 5 to 40 mm.

Figure 31:
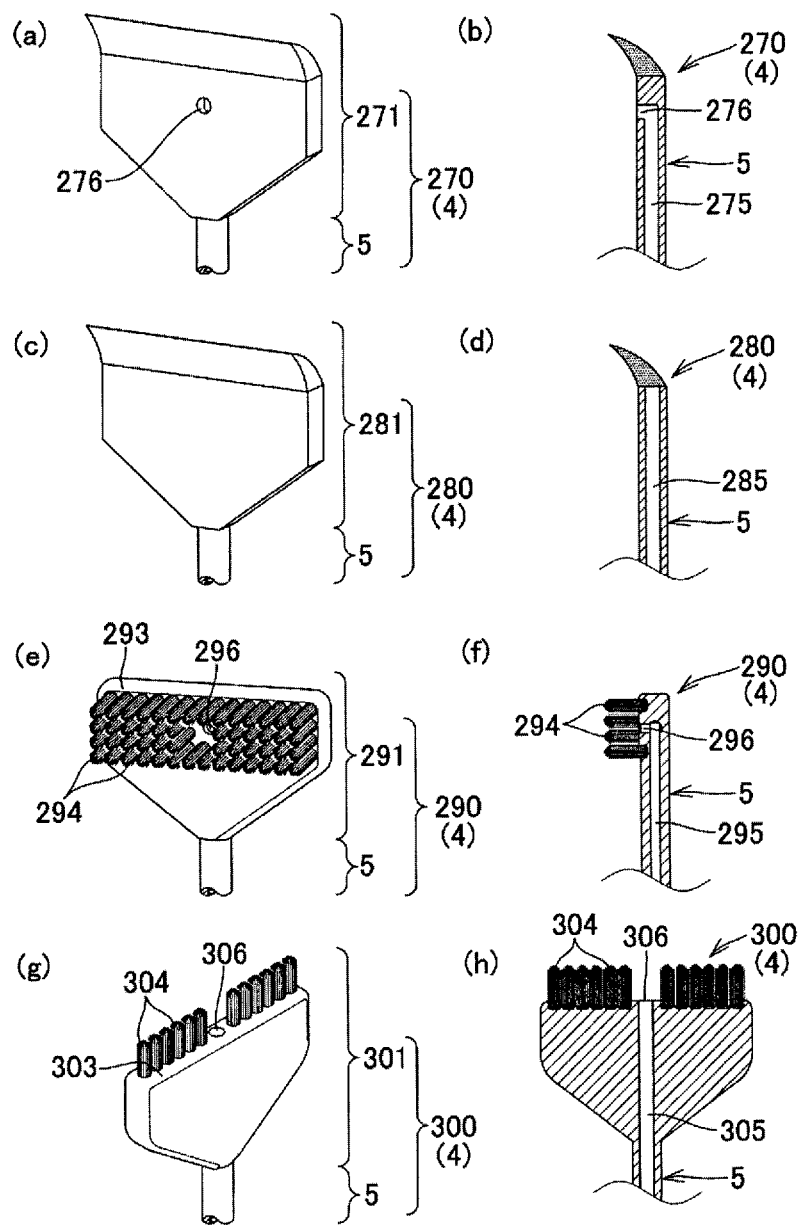
FIG. 31(a) to FIG. 31(h) are perspective views and vertical cross-sectional views showing a tongue cleaner body.

FIG. 31 shows examples in which a personal hygiene body 4 is a tongue cleaner body 270, 280, 290, and 300 in which a personal hygiene section is a tongue cleaner body 271, 281, 291, and 301 for performing cleaning and sterilization of a tongue. In the example in FIG. 31(a) and FIG. 31(b), the tongue cleaner section 271 consists of a scrubbing and sweeping member composed of an elastic body such as elastomer and the like. A flow passageway 275 for flowing the drug in an axial direction is formed in the interior of a shaft section 5 and a discharge opening 276 for discharging the drug is open on the tongue cleaner section 271. In an example in FIG. 31(c) and FIG. 31(d), a configuration is such that a porous member such as a sponge is provided at a distal end of a tongue cleaner section 281, and a flow passageway 285 in the interior of the shaft section 5 is connected thereto, the drug leaches from the porous member.

In an example in FIG. 31(e) and FIG. 31(f), the tongue cleaner section 291 has brush hair 294 having filaments implemented in a wide side, and on the side, a discharge opening 296 in communication with the flow passageway 295 of the shaft section 5 is open. Although filaments for hair implantation are not specifically limited as far as they can be used, they include, for example, synthetic resins such as nylon, polyester, acryl, vinylon, polybuthylene terephthalate and the like, recycled fibers such as rayon, acetate and the like, natural fibers such as wool, silk, cotton, linen and the like. In the example shown in FIG. 31(g) and FIG. 31(h), similarly, the tongue cleaner section 291 has brush hair 304 consisting of implanted filaments on the distal-end surface and has the discharge opening 306 in communication with the flow passageway 295 of the shaft section 5 on the side surface. Although width of these tongue cleaners can be set arbitrarily, it is preferably 10 mm to 30 mm. In addition, shape of the discharge opening can also be arbitrarily set to a slit hole or one or more holes and the like.

Figure 32:
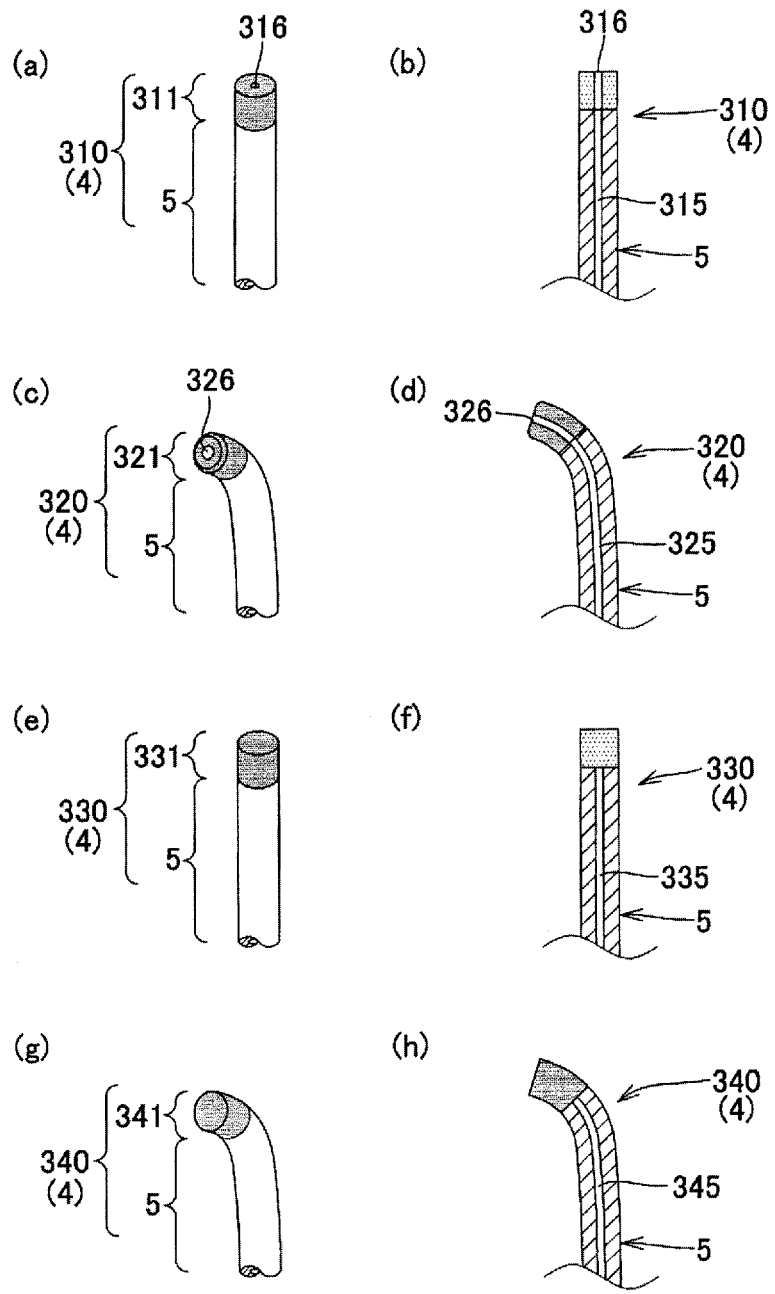
FIG. 32(a) to FIG. 32(h) are perspective views and vertical cross-sectional views showing a tooth surface cleaning body.

FIG. 32 shows examples in which a personal hygiene body 4 is a tooth surface cleaning body (tooth surface eraser) 310, 320, 330, and 340 in which a personal hygiene section 311, 321, 331, and 341 is a tooth surface cleaning section for performing cleaning of a tooth surface. Such a tooth surface cleaning body has a shaft section 5 made from synthetic resin such as polyethylene, polypropylene and the like to which a tooth surface cleaning section (eraser section) 311, 321, 331, and 341 made from an elastic body such as silicon rubber and the like is adhered.

In an example shown in FIG. 32(a) to FIG. 32(d), flow passageways 315, 325 for axially flowing a drug 2 are internally formed from the shaft section 5 to the tooth surface cleaning sections 311, 321, and discharge openings 316, 326 for discharging the drug 2 to a distal-end surface of the tooth surface cleaning sections 311, 321 are formed. FIG. 32(a) and FIG. 32(b) illustrate those having a straight shape by example. FIG. 32(c) and FIG. 32(d) illustrate those having a curved shape by example. Although the outer diameter of the shaft section 5 and tooth surface cleaning sections 311, 321 can be arbitrarily set, it is preferably 3 mm to 10 mm. In addition, the inner diameter of the internal flow passageways 315, 325 can also be arbitrarily set, it is preferably 0.4 mm to 1.0 mm. FIG. 32(e) to FIG. 32(h) are configured such that a porous member such as a sponge is provided as a tooth surface cleaning section 331, 341, flow passageways 335, 345 in the interior of the shaft section 5 are connected thereto, and the drug oozes from the porous member.

Figure 33:
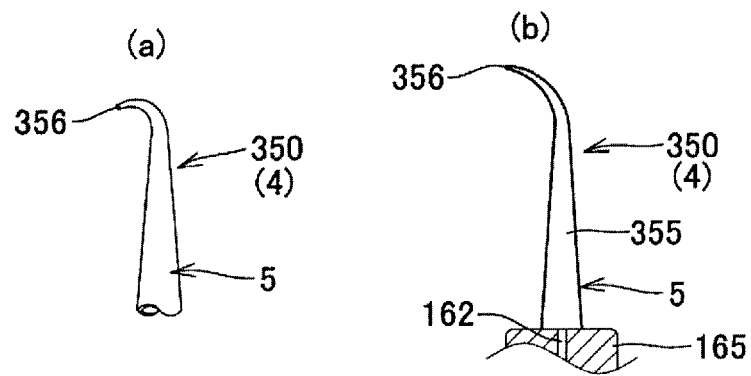
FIG. 33(a) and FIG. 33(b) are a perspective view and vertical cross-sectional view showing a toothpick body.

FIG. 33 shows examples in which a personal hygiene body 4 is a toothpick body (interdental insert) 350 in which a personal hygiene section is a drug discharge section 356 that discharges the drug between teeth to perform cleaning. The toothpick body 350 comprises a hollow shaped shaft section 5 whose distal end is tapered and bent, and the interior of the shaft section 5 constitutes a flow passageway 355 through which the drug 2 flows. The inner diameter of the distal-end discharge opening is preferably 0.4 mm to 1.0 mm. The toothpick body 350 is made from synthetic resin such as polyethylene, polypropylene, acrylonitrile and the like. The length of the toothpick body 350 is desirably 10 mm to 30 mm.

Figure 34:
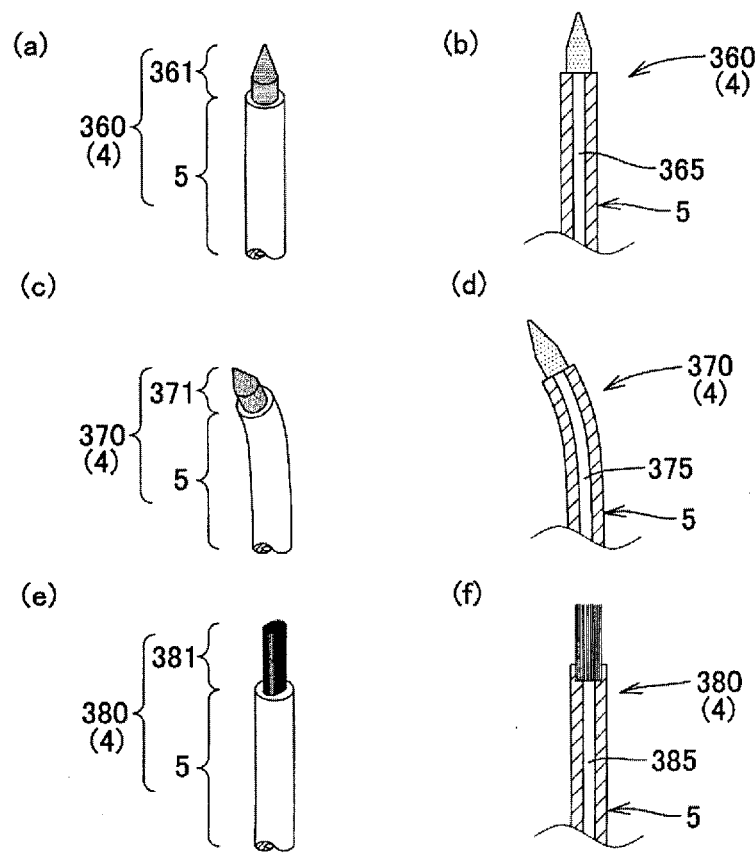
FIG. 34(a) to FIG. 34(f) are perspective views and vertical cross-sectional views showing a drug application body.
Figure 35:
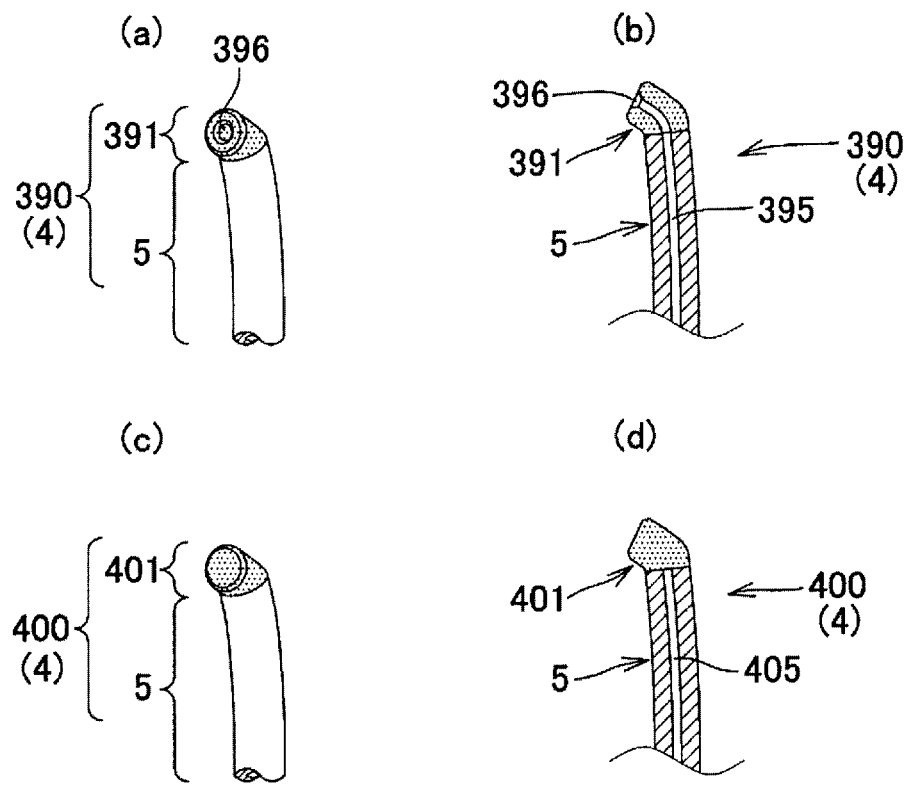
FIG. 35(a) to FIG. 35(d) are perspective views and vertical cross-sectional views showing a drug application body.

FIG. 34 and FIG. 35 show examples in which a personal hygiene body 4 is a drug application body 360, 370, 380, 390, 400, and 410 in which a personal hygiene section is a drug application section 361, 371, 381, 391, 401, and 411 for performing interdental cleaning or application of the drug. FIG. 34(a) to FIG. 34(d) have a distal end of a shaft section 5 made from synthetic resin such as polyethylene and polypropylene to which a felt is adhered by an adhesive as the drug application section 361, 371. In addition to the felt, a porous member such as a sponge and nonwoven fabric may be used for the drug application section 361, 371. The maximum diameter of the drug application section 361, 371 is preferably 3 mm to 10 mm. In the interior of the shaft section 5, flow passageways 365, 375 for axially flowing the drug toward the drug application section 361, 371 are formed. The inner diameter of the flow passageways 365, 371 is preferably 0.4 mm to 1.0 mm.

FIG. 34(*e*) and FIG. 34(*f*) show an example in which a drug application section 381 is formed by filament implantation. The drug application section 381 is, for example, composed of bundled hair made from synthetic resin such as polyethylene, polypropylene and the like implanted at a distal end of a shaft section 5. Although fibers for hair implantation are not specifically limited, they include, for example, synthetic resin such as nylon, polyester, acryl, vinylon, and polybuthylene terephthalate, recycled fibers such as rayon and acetate, natural fibers such as wool, silk, cotton, and linen, and the like. In FIG. 35(*a*) to FIG. 35(*d*), a drug application section 391, 401 made of sponge is adhered to a distal end of a shaft section 5 made from synthetic resin such as polyethylene and polypropylene, by an adhesive. In addition to the sponge, a porous member such as urethane and nonwoven fabric and the like may be used for the drug application section 391. The maximum diameter of the drug application section 361 is preferably 3 mm to 10 mm. In the example of FIG. 35(*a*) and FIG. 35(*b*), through-bores 395 for axially flowing the drug 2 are continuously formed in the interior of the shaft section 5 to the drug application section 391, and a discharge opening 396 for discharging the drug 2 is provided on a distal-end surface of the drug application section 391. The inner diameter of the flow passageway 365 is preferably from 0.4 mm to 1.0 mm.

Figure 36:
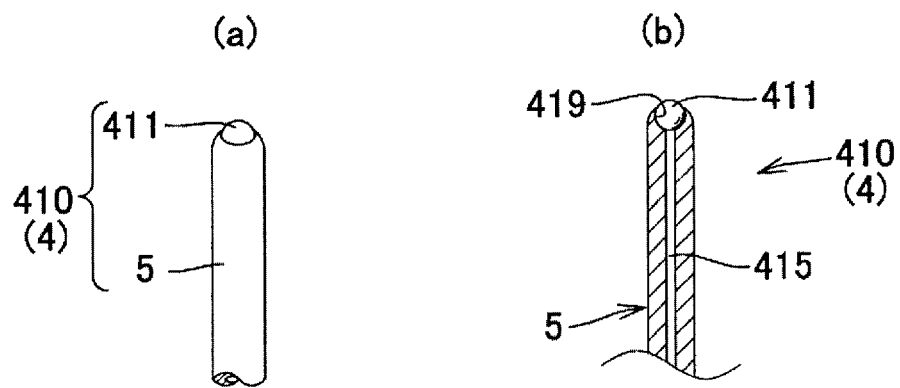
FIG. 36(a) and FIG. 36(b) are a perspective view and vertical cross-sectional view of a drug application body.

FIG. 36 shows examples of a personal hygiene body 4 in which a personal hygiene section is a roll-on type drug application body for performing drug application. At a distal end of a shaft section 5 of a drug application body 410 are provided a ball 411 to which a drug 2 is attached and a retainer 419 which keeps the ball 411 rotatable while keeping one part of the ball exposed to the exterior and being able to bring other part into contact with the drug 2 in the container. The ball 411 is composed of resin or metal, and a diameter of the ball 411 is preferably 1 mm to 10 mm. An applicator shaft section 5 of a roll-on drug applicator 410 has a flow passageway 415 for axially flowing the drug toward the ball 411 in the interior thereof. The inner diameter of the flow passageway 415 is preferably 0.4 mm to 5 mm.

Figure 37:
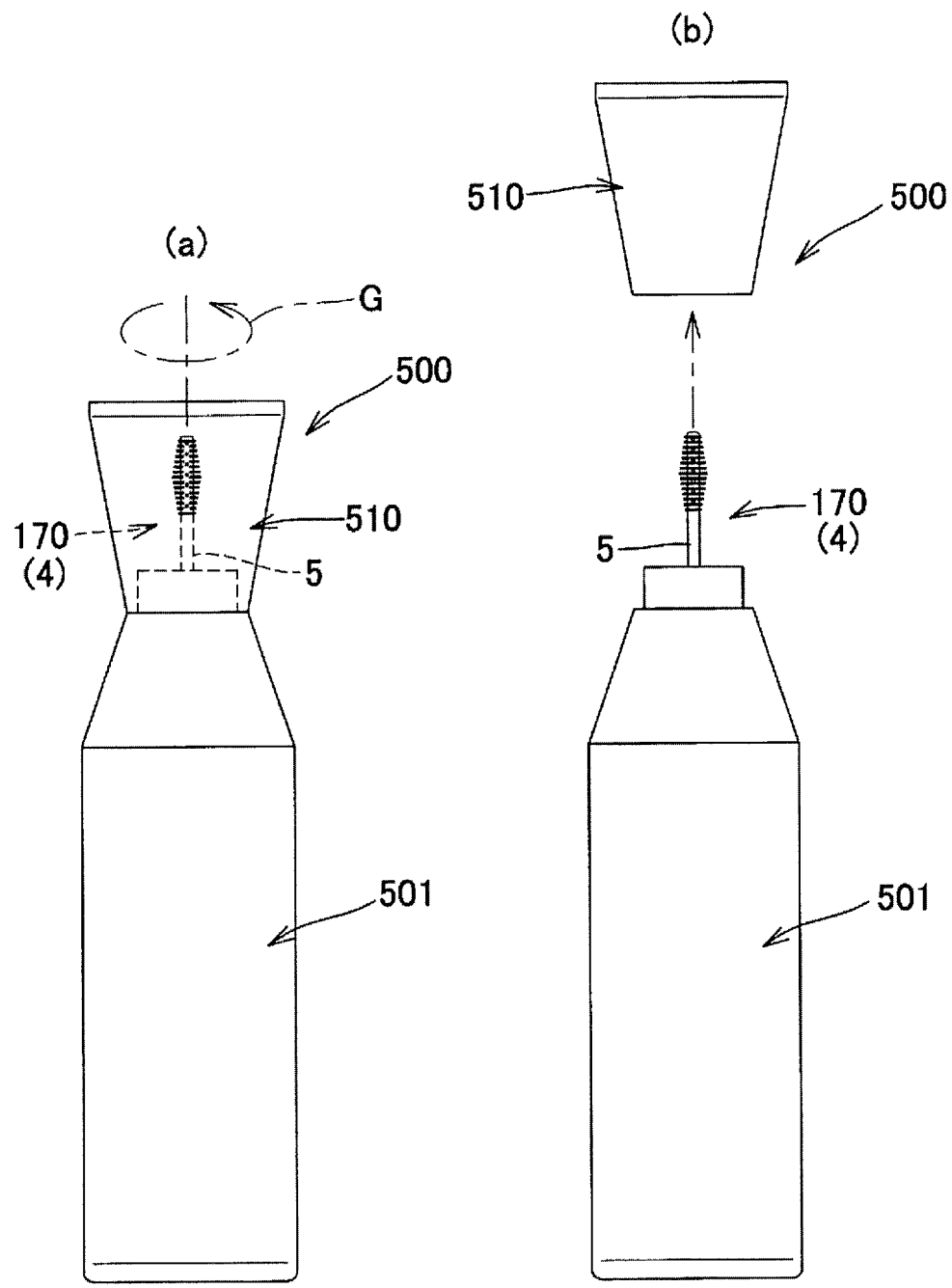
FIG. 37(a) and FIG. 37(b) are explanatory drawings of a drug-containing personal hygiene implement according to a fourth embodiment of the present invention.

Based on FIG. 37 and FIG. 38, a fourth embodiment of the present invention will be described in the following.

A drug-containing personal hygiene implement 500 of the embodiment is designed to enable discharging of a drug by opening operation of twisting off a base end section of a cap body 510 to separate it from a bottle body 501, and includes the bottle body 501 in which the drug 2 is stored, an interdental brush body 170, which is a personal hygiene body 4 protruding at a distal end of the bottle body 501 in an axial line direction of the bottle body 501, and the cap body 510 attached to the distal end of the bottle body 501 and covering the interdental brush body 170. Similar to the first embodiment, the drug-containing personal hygiene implement 500 of the embodiment is manufactured by a sterile filling and packaging manufacturing machine in a series of blow-fill-seal (BFS) processes, and a sterile drug can be manufactured in a sterile container in a sterile environment. Thus, this enables long-term storage of drugs without blending preservatives such as paraben or alcohol, also making it possible to manufacture a drug-containing personal hygiene implement of disposable type with no preservative blended.

Figure 38:
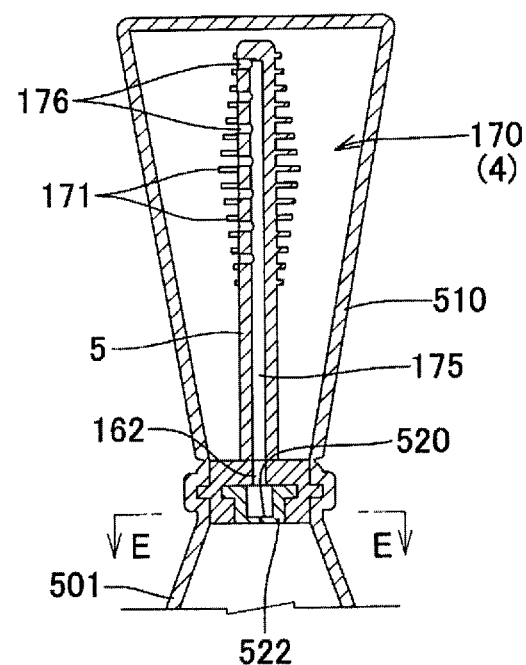
FIG. 38(a) is a vertical cross-sectional view of a main part of the same drug-containing personal hygiene implement.
FIG. 38(b) is a transverse cross-sectional view of E-E of FIG. 38(a).
Figure 38:
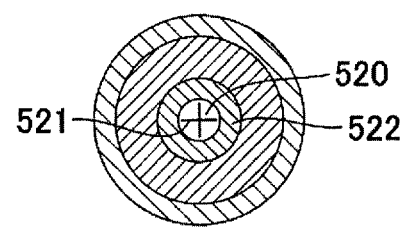

As shown in FIG. 38(*a*), at the distal end of the bottle body 501 is provided a through-hole 162 for guiding the drug 2 in communication with the flow passageway 175 in the shaft section 5 of the interdental brush body 170, and by opening operation of twisting off the base end section of the cap body 510 to separate it from the bottle body 501, the interior of the cap body 510 is no longer air-tight state, and the atmospheric pressure balance is lost, thereby enabling the drug 2 to be discharged. Via the through-hole 162, the drug 2 stored in the bottle body 501 is supplied to the interdental brush section through the flow passageway 175 and a discharge path 176. Also in this example, as shown in FIG. 38(*b*), a slit valve 520 composed of a silicon valve is provided so as to block the through-hole 162. With the slit valve 520, the drug does not easily leak even if the bottle body 501 is inadvertently pressed before opening, and even after opening, discharging of the drug 2 in large amounts when the bottle body 501 is strongly pressed can be prevented, thereby making it easy to adjust the amount of discharge.

The slit valve 520 is formed by cutting an opening/closing slit 521 like a cross, for example, and integrally molded at the distal end of the bottle body 501 together with a valve retaining member 522. Then, when the stored drug 2 is extracted from the discharge path 176 by pressing a base of the bottle body 501, the slit valve 520 projects upwards due to the extraction pressure, and opens the slit 521 to extract the drug. On the other hand, if pressure on the base of the bottle body is released to stop extraction of the drug 2, the slit valve 520 closes the slit 521.

A material of the bottle body 501 and a drug in the interior thereof can be the same as the bottle body and drug of the first to third embodiments. In addition, the interdental brush body 170, which is the personal hygiene body 4, is also the same as that of the third embodiment described above, and the same symbols are assigned to the same structures, a description of which is omitted. In addition, in this embodiment, although the personal hygiene body is the interdental brush body 170 in which the personal hygiene section is the interdental brush section 171, similar to the third embodiment, other form may be acceptable. For example, as illustrated in FIG. 30 to FIG. 37, the personal hygiene body can be a toothbrush body in which the personal hygiene section is a toothbrush section, a tongue cleaner body in which the personal hygiene section is a tongue cleaner section, a toothpick body in which the personal hygiene section is a tapered drug discharge section, a tooth surface cleaning body in which the personal hygiene section is a tooth surface cleaning section, or a drug application body in which the personal hygiene section is a drug application section. Then, the drug is supplied to the personal hygiene section through the flow passageway in the interior of the shaft section in these forms and discharged from the discharge opening. In addition, similar to the first embodiment, the personal hygiene implement can be attached to a holder as shown in FIG. 21 to FIG. 24. Then, after opening by twisting off the cap body 10A, it can be attached to the holder.

In the configurations described in the first embodiment to the fourth embodiment and variants described above, some configuration may be exchanged as appropriate as far as they are consistent. These variants can also achieve similar effects to the embodiments described above.

The invention claimed is:

1. A drug-containing personal hygiene implement, comprising:
   a bottle body in which a drug is stored; and a personal hygiene body which has a shaft section and a distal-end side personal hygiene section, protrudes to a distal-end side of the bottle body, and is used to implement care of a human body;
wherein a tubular protrusion which tubularly projects to cover the shaft section of the personal hygiene body is provided at the distal-end section of the bottle body, and a passage for guiding the drug to a distal-end side of the tubular protrusion is provided at an inner side of the tubular protrusion, said passage guiding the stored drug to the personal hygiene body;
wherein by opening operation, the passage in the interior of the bottle body enables the drug to flow therethrough,
further comprising a cap body covering the personal hygiene body, wherein a base end section of the cap body is installed consecutively with the distal-end section of the bottle body so as to block the passage; and
by opening operation of twisting off the base end section of the cap body to separate it from the bottle body, a discharge opening of the passage is formed.

2. The drug-containing personal hygiene implement according to claim 1, wherein the personal hygiene body is an interdental brush body in which the personal hygiene section is an interdental brush section, a toothbrush body in which the personal hygiene section is a toothbrush section, or a tongue cleaner body in which the personal hygiene section is a tongue cleaner section; and wherein the drug is supplied to the personal hygiene section along the outer surface of the shaft section.

3. A drug-containing personal hygiene implement, comprising:
a bottle body in which a drug is stored; and
a personal hygiene body which has a shaft section and a distal-end side personal hygiene section, protrudes to a distal-end side of the bottle body, and is used to implement care of a human body;
wherein a tubular protrusion which tubularly projects to cover the shaft section of the personal hygiene body is provided at the distal-end section of the bottle body, and a passage for guiding the drug to a distal-end side of the tubular protrusion is provided at an inner side of the tubular protrusion, said passage guiding the stored drug to the personal hygiene body;
wherein by opening operation, the passage in the interior of the bottle body enables the drug to flow therethrough,
wherein the implement is provided with a holder having a holder main body section capable of storing the bottle body and composed of hard material and a holder cap section covering the personal hygiene body and similarly composed of hard material;
the holder main body section has an opening, through which the bottle body to be stored can be pressed with fingers from the side, provided on a surrounding wall; and
the holder cap section is detachably provided at a distal-end section of the holder main body section.

4. A drug-containing personal hygiene implement, comprising:
a bottle body in which a drug is stored; and
a personal hygiene body which has a shaft section and a distal-end side personal hygiene section, protrudes to a distal-end side of the bottle body, and is used to implement care of a human body;
wherein a tubular protrusion which tubularly projects to cover the shaft section of the personal hygiene body is provided at the distal-end section of the bottle body, and a passage for guiding the drug to a distal-end side of the tubular protrusion is provided at an inner side of the tubular protrusion, said passage guiding the stored drug to the personal hygiene body;
wherein by opening operation, the passage in the interior of the bottle body enables the drug to flow therethrough,
wherein the implement is provided with a holder having a holder main body section capable of storing the bottle body and composed of hard material and a holder cap section covering the personal hygiene body and similarly composed of hard material;
the holder main body section is provided with a pressing mechanism which presses and compresses the bottle body to be stored from the base end side with a pressing member; and
the holder cap section is detachably provided at the distal-end section of the holder main body section.

5. The drug-containing personal hygiene implement according to claim 4, wherein
the pressing mechanism comprises a screw rod built in the base end side of the holder main body section, the pressing member threaded onto the screw rod and mounted to be not rotatable to the inner wall of the holder main body section and movable to an axial direction, and an operating member for rotating and operating the screw rod.

6. The drug-containing personal hygiene implement according to claim 4, wherein
the bottle body is configured to be in a bellows shape which can be freely compressed or deformed in the axial direction.

7. A drug-containing personal hygiene implement, comprising:
a bottle body having a seal section provided at a distal end of a neck section, and the drug being stored in the interior thereof in a hermetically-sealed state;
a cap member attached to the neck section of the bottle body; and
a personal hygiene body which has a shaft section and a distal-end side personal hygiene section, protrudes to an outer surface side of the cap member, and is used to implement care of a human body; wherein
a tubular protrusion which tubularly projects to cover the shaft section of the personal hygiene body is provided at an outer surface side of the cap member;
a protrusion is provided on the inner surface side of the cap member facing the seal section of the bottle body;
a through-hole for drug distribution in communication with the inner surface side of the cap member to the inner side of the tubular protrusion is provided; and
by opening operation of attaching the cap member to the neck section of the bottle body, the protrusion penetrates the seal section, thereby making it possible to supply the drug in the bottle body to the inner side of the tubular protrusion via the through-hole.

8. The drug-containing personal hygiene implement according to claim 7, wherein the inner side of the tubular protrusion is formed as a trap section for the drug.

9. The drug-containing personal hygiene implement according to claim 7, wherein the through-hole leads from the protrusion of the cap member to the outer surface side of the cap member.

* * * * *